(12) United States Patent
Chinitz et al.

(10) Patent No.: US 7,702,468 B2
(45) Date of Patent: Apr. 20, 2010

(54) EVALUATING GENETIC DISORDERS

(75) Inventors: James Chinitz, Dix Hills, NY (US); Eli Hatchwell, Cold Spring Harbor, NY (US)

(73) Assignee: Population Diagnostics, Inc., Melville, NY (US)

( * ) Notice: Subject to any disclaimer, the term of this patent is extended or adjusted under 35 U.S.C. 154(b) by 505 days.

(21) Appl. No.: 11/421,348

(22) Filed: May 31, 2006

(65) Prior Publication Data

US 2007/0259351 A1 Nov. 8, 2007

Related U.S. Application Data

(60) Provisional application No. 60/746,359, filed on May 3, 2006, provisional application No. 60/746,482, filed on May 4, 2006.

(51) Int. Cl.
G06F 7/00 (2006.01)

(52) U.S. Cl. ............................. 702/19; 702/20; 703/11; 707/102; 435/6; 436/501

(58) Field of Classification Search .................. 702/19, 702/20; 703/11; 707/102; 435/6; 436/501
See application file for complete search history.

(56) References Cited

U.S. PATENT DOCUMENTS

| | | | |
|---|---|---|---|
| 5,665,549 A * | 9/1997 | Pinkel et al. ................... | 435/6 |
| 6,210,878 B1 * | 4/2001 | Pinkel et al. ................... | 435/6 |
| 7,424,368 B2 * | 9/2008 | Huang et al. ................... | 702/19 |
| 2003/0049663 A1 | 3/2003 | Wigler et al. | |
| 2003/0082606 A1 * | 5/2003 | Lebo et al. ...................... | 435/6 |
| 2004/0137473 A1 | 7/2004 | Wigler et al. | |
| 2004/0197774 A1 | 10/2004 | Wigler et al. | |
| 2005/0032095 A1 | 2/2005 | Wigler et al. | |
| 2005/0037393 A1 | 2/2005 | Gunderson et al. | |
| 2005/0112595 A1 | 5/2005 | Zhao et al. | |
| 2005/0196799 A1 | 9/2005 | Wigler et al. | |
| 2005/0233339 A1 | 10/2005 | Barrett et al. | |
| 2005/0266444 A1 | 12/2005 | Wigler et al. | |
| 2006/0063168 A1 * | 3/2006 | Albertson et al. ............... | 435/6 |
| 2006/0134674 A1 | 6/2006 | Huang et al. | |
| 2007/0207481 A1 | 9/2007 | Wigler et al. | |

FOREIGN PATENT DOCUMENTS

WO WO 2007/070640 6/2007
WO WO 2007/129000 * 11/2007
WO WO 2008/016374 2/2008

OTHER PUBLICATIONS

Hatchwell, et al. High rate of submicroscopic human genomic polymorphism detected by array CGH. Proceedings of XIX International Genetics Congress. Melbourne, Australia. Abstracts and Posters. 2003; 1.E.0092. pp. 168 and 319.

Gilling, et al. Breakpoint cloning and haplotype analysis indicate a single origin of the common Inv(10)(p11.2q21.2) mutation among northern Europeans. *Am. J. Hum. Genet.* 2006; 78(5):878-83.

Gribble, et al. The complex nature of constitutional de novo apparently balanced translocations in patients presenting with abnormal phenotypes. *J. Med. Genet.* 2005; 42:8-16.

Harada, et al. Subtelomere specific microarray based comparative genomic hybridisation: a rapid detection system for cryptic rearrangements in idiopathic mental retardation. *J. Med. Genet.* 2004; 41:130-136.

Iafrate, et al. Detection of large-scale variation in the human genome. *Nature Genet.* 2004; 36:949-51.

Jorde, et al. Population genomics: a bridge from evolutionary history to genetic medicine. *Hum. Mol. Genet.* 2001; 10(20):2199-2207.

Pinkel, et al. Comparative genomic hybridization. *Annu. Rev. Genomics Hum. Genet.* 2005; 6:331-54.

Pollack, et al. Microarray analysis reveals a major direct role of DNA copy number alteration in the transcriptional program of human breast tumors. *Proc. Natl. Acad. Sci.* 2002; 99(20):12963-68.

Sebat, et al. Large-scale copy number polymorphism in the human genome. *Science.* 2004; 305(5683):525-8.

Snijders, et al. Assembly of microarrays for genome-wide measurement of DNA copy number. *Nature Genet.* 2001; 29:263-264.

Vissers, et al. Array-based comparative genomic hybridization for the genomewide detection of submicroscopic chromosomal abnormalities. *Am. J. Hum. Genet.* 2003; 73:1261-70.

Bailey, et al. Analysis of Segmental Duplications and Genome Assembly in the Mouse. *Genome Res.* 2004; 14:789-801.

Hicks et al., "Novel patterns of genome rearrangement and their association with survival in breast cancer," Genome Res 16:1465-1479, 2006.

(Continued)

*Primary Examiner*—Mary K Zeman
(74) *Attorney, Agent, or Firm*—Wilson Sonsini Goodrich & Rosati PC

(57) ABSTRACT

The present invention relates to genetic analysis and evaluation utilizing copy-number variants or polymorphisms. The methods utilize array comparative genomic hybridization and PCR assays to identify the significance of copy number variations in a subject or subject group.

25 Claims, 3 Drawing Sheets

OTHER PUBLICATIONS

Aitman, et al. Copy number polymorphism in Fcgr3 predisposes to glomerulonephritis in rats and humans. Nature. Feb. 16, 2006;439(7078):851-5.

Cronin, et al. Analysis of genome-wide copy number variation in Irish and Dutch ALS populations. Hum Mol Genet. Nov. 1, 2008;17(21):3392-8. Epub Aug. 7, 2008.

Dibbens, et al. Familial and sporadic 15q13.3 microdeletions in Idiopathic Generalized Epilepsy: Precedent for Disorders with Complex Inheritance. Hum Mol Genet. Jul. 10, 2009. Epub ahead of print.

Glessner, et al. Autism genome-wide copy number variation reveals ubiquitin and neuronal genes. Nature. May 28, 2009;459(7246):569-73. Epub Apr. 28, 2009.

Kumar, et al. A de novo 1p34.2 microdeletion identifies the synaptic vesicle gene RIMS3 as a novel candidate for autism. J Med Genet. Jun. 21, 2009. Epub ahead of print.

Roohi, et al. Disruption of contactin 4 in three subjects with autism spectrum disorder. J Med Genet. Mar. 2009;46(3):176-82.

Snijders, et al. Mapping segmental and sequence variations among laboratory mice using BAC array CGH. Genome Res. Feb. 2005;15(2):302-11.

Stefansson, et al. Large recurrent microdeletions associated with schizophrenia. Nature. Sep. 11, 2008;455(7210):232-6.

Summary of NRSP-8 Accomplishments: 2003-2008. Available at http://www.lgu.umd.edu/lgu_v2/pages/attachs/ 9956_Attach1%20%202003-08%20ACCOMPLISHMENTS.doc. Published on Feb. 9, 2008. (6 pages).

The International Schizophrenia Consortium. Rare chromosomal deletions and duplications increase risk of schizophrenia. Nature. Sep. 11, 2008;455(7210):237-41. Epub Jul. 30, 2008.

Weiss, et al. Association between microdeletion and microduplication at 16p11.2 and autism. N Engl J Med. Feb. 14, 2008;358(7):667-75.

\* cited by examiner

EVALUATING GENETIC DISORDERS

CROSS-REFERENCE

This application claims the benefit of U.S. Provisional Application Nos. 60/746,359 and 60/746,482 filed May 3, 2006 and May 4, 2006 respectively, which are incorporated herein by reference in there entirety.

TECHNICAL FIELD

This invention is in the field of genetics, diagnostics and treatment. Specifically, the invention relates to the discovery and characterization of genetic abnormalities. In addition, the invention encompasses the generation and utilization of databases, i.e., knowledge management tools, to screen and identify drug treatments tailored specifically for an individual or for a particular cohort of individuals. The compositions and methods embodied in the present invention are particularly useful in identifying microscopic and submicroscopic genome variations, including deletions, duplications and large-scale polymorphisms, so as to gauge genomes for variations associated with normal and disease states.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Altered DNA copy number is one of the many ways that gene expression and function may be modified. Some variations are found among normal individuals, others occur in the course of normal processes in some species, and still others participate in causing various disease states. For example, many defects in human development are due to gains and losses of chromosomes and chromosomal segments that occur prior to or shortly after fertilization, whereas DNA dosage alterations that occur in somatic cells are frequent contributors to cancer. Therefore, detection of such aberrations, and interpreting them within the context of broader knowledge, facilitates identification of critical genes and pathways involved in biological processes and diseases, and provides clinically relevant information, such as in identifying efficacious drug regimes.

One obstacle in medical genetics has proven to be "ascertainment bias", which refers to an inherent skewing ascribed to data, because of the manner in which such data is collected. Several examples of ascertainment bias are known. Indeed, many of the 'classical' patients described in the relevant art actually represent the more severe end of the spectrum, because such patients were much more likely to seek medical attention and therefore be observed. For example, the classical descriptions of patients with Klinefelter syndrome (47, XXY) depict a mentally retarded male with gynecomastia (breast development) and infertility. In fact, however, an unbiased population survey reveals that 1:1,000 men have this syndrome and 80% of them have neither significant mental retardation nor gynecomastia (although all are infertile). Similarly, it was originally determined that the majority of females with Turner syndrome (45, X0) had mental retardation. However, this determination was also proven false, as those in the art had identified only the most severely affected patients. Indeed, because of ascertainment bias, cytogeneticists conducted large studies on unselected newborns, so that the true rate of chromosomal abnormalities could be more rigorously investigated. Of course such studies required prohibitively labor and time intensive cytogenetic analysis, but the researchers realized that data must be obtained from a relatively large number of individuals to provide a reference population.

Conceptual and technical developments in molecular cytogenetics are now enhancing the resolving power of conventional chromosome analysis techniques to levels that are unprecedented. Over the past several years array comparative genomic hybridization (array CGH) has demonstrated its value for analyzing DNA copy number variations. Array CGH (Comparative Genomic Hybridization), is a new technology that has the capacity of examining chromosomes at a much higher resolution than standard cytogenetics techniques. It is clear that array CGH technology will emerge as the dominant tool for diagnostics in the 21st century: a fundamental requirement for every cytogenetics and diagnostic reference lab as well as for the researchers focused on genetic research within academia, biotechnology and pharmaceutical industries.

Copy-number variation presents an important opportunity in medical genetics. The importance of normal copy-number variation involving large segments of DNA has been unappreciated, until now. Although array CGH has established the existence of copy number polymorphisms in the human genome, the picture of this normal variation is incomplete. In results reported to date, measurement noise has restricted detection to polymorphisms that involve genomic segments of many kilobases or larger, genome coverage has been far from comprehensive, and the population has not been adequately sampled.

A comprehensive understanding of these normal variations is of intrinsic biological interest and is essential for the proper interpretation of array CGH data and its relation to phenotype. Furthermore, understanding the copy number polymorphisms that are detectable by a particular array CGH technique is important so that normal variations are not falsely associated with disease, and, conversely, to determine if some so-called normal variation may underlie phenotypic characteristics such as disease susceptibility.

As such, the intense utilization of array CGH technology is driving the essential need for understanding normal variation throughout the human population. The present invention provides compositions and methods that fill this unmet need for understanding normal variation thus facilitating personalized genetic based evaluation and treatment. However, copy number abnormalities or variations currently represent an enormous untapped opportunity in the field of predictive personalized medicine. These copy number variations, also called copy number polymorphisms, occur in both normal situations as a part of the changes that have occurred within populations of individuals but also occur in disease states. Being able to distinguish between normal copy variations and those associated with a disease would permit a more accurate diagnosis based on a genetic analysis.

It is believed that copy number abnormalities are key genetic components which will be used to diagnose disease, as well as differentiate pharmaceuticals for drug efficacy and adverse reactions in an individual. Since many disorders can be associated in at least some cases with very rare variants, it is necessary for the size of the database utilized for such genetic analysis to be large. Utilizing a smaller database can provide absolutely incorrect results leading to erroneous diagnosis and treatment.

For example, a chromosome 8q24.3 microdeletion was first detected in a patient with a rare pediatric syndrome, Kabuki Make Up syndrome. The investigators at the time did not yet appreciate how frequent such variants were. Kabuki make-up syndrome (KMS) is a multiple malformation/mental retardation syndrome that was described initially in Japan but is now known to occur in many other ethnic groups. However, the immediate temptation was to conclude that this variant was associated with the disorder being investigated. Further investigations revealed the microdeletion to be present in a small percentage of Caucasians, none of whom suffered from Kabuki syndrome. There have been 13 chromosomal abnormalities associated with KMS. However, no common abnormalities or breakpoints that possibly contribute to positional cloning of the putative KMS gene(s) are known (Matsumoto et al. 2003). Although clinical manifestations of KMS are well established, its natural history, useful for genetic counseling, remains to be studied.

Because of the magnitude of the number of variations that exist in the genetic material and the existence of normal copy number abnormalities, sophisticated analysis tools are required to interpret the results of any genetic evaluation. There is thus the need for methods, and tools, such as variation knowledge management tools of the present invention, to permit an accurate diagnosis of a sub-microscopic chromosomal variant.

SUMMARY OF THE INVENTION

There are five core aspects of the present invention driven by the engine of the normal variation knowledge management tools. Although all five core aspects rely on the use of the normal variation knowledge management tools (KMTs), the aspects are mutually exclusive. The core aspects are: 1. Diagnostic Tests and Diagnostic Certainty Services; 2. Research and Research Services; 3. Translational Medicine; 4. Predictive and Personalized Medicine; and 5. Life Sciences Tools.

The present invention provides compositions and methods for generating and utilizing Normal Variation KMTs, comprehensive relational databases and suites of software tools derived from internal methodologies of array CGH technology, thus making universal tools for the field at large. One embodiment of the invention provides compositions and methods that essentially eliminate the subjective nature of interpreting chromosomal changes so that the technology field as a whole can rely on array CGH derived data in both research and diagnostic environments ("bench to bedside"). By providing information on copy number variations from thousands of individuals, the KMTs remove the subjective interpretation of array CGH data and provide a means for securing the medically relevant consensus of a biomarker amongst physicians within the prescribing community. In other words, the KMTs enable a clinician to actually determine the significance of a copy number variation detected in a subject (e.g., patient needing treatment or subject for diagnostic purposes).

The KMTs perform this function by providing population frequencies of copy number changes and association data between certain copy number changes and certain phenotypes and disease states, genomic annotation in terms of gene content and known disorders. There are two KMTs, the normal copy number variation database and a copy number breakpoint map, provided as software and/or a computer system for comparing information derived from the genome of subjects against the KMTs to determine the significance of any copy number polymorphisms present.

In addition to aCGH, PCR assays are utilized to study copy number variation and as well as analyze a number of these variants at a molecular level. An embodiment of the invention also provides several products that are utilized in one or more methods described herein. The products include software on a computer readable medium for programming a computer to perform the comparison of test information from subjects against the KMTs, computer systems for doing such comparisons, CGH arrays for running the analysis of the subject's genome, and reagents and downstream analysis components, such as requests for performing analyses for biomarkers of significance that are related to diseases or conditions identified utilizing the KMTs of the invention.

An aspect of the invention includes utilizing the KMTs in pharmacogenomics, toxicogenomics and genetic counseling by associating the identified relevant copy number polymorphisms and the effectiveness or adverse effects of therapeutics. Such relevance and association creates personalized medicine by linking an individual's genome to more successful administration of pharmaceuticals. This linkage also permits the rescue of pharmaceuticals from clinical trials by identifying subpopulations of individuals for whom the therapeutic is useful based on the comparison of the genomic variations to the KMTs of the invention.

In one embodiment, a database for normal copy number variants is compiled and corresponds to genome-wide analysis for a large population of subjects comprising hundreds or thousands or at least 10,000 subjects. In another embodiment, a database of normal copy number variants is compiled for each of multiple cohorts of subjects, wherein each cohort represents an ethnic group, and whereby each database provides genome-wide analysis for very large groups comprising thousands or at least 10,000 subjects. As used herein an "ethnic group" includes any of the known human ethnic groups, including subgroups where desired, where an ethnic group is a human population whose members identify with each other, usually on the basis of a presumed common genealogy or ancestry (Smith 1986). Ethnic groups are also usually united by common cultural, behavioural, linguistic, or religious practices. In this sense, an ethnic group is also a cultural community.

From an objective standpoint, an ethnic group is also an endogamous population, that is, members of an ethnic group procreate primarily with other members of their ethnic group, something which is measurable in terms of characteristic average genetic frequencies. These differences, however, usually do not approach the magnitude of racial difference in that the genetic differences within an ethnic group are greater than the difference between any two ethnic groups. The characteristic of endogamy is reinforced by proximity, cultural familiarity, and also social pressure (in extreme cases, by legal command) to procreate within the ethnic group. Examples of ethnic groups include White, Black, Hispanic, Asian, Middle Eastern, Jewish, or Shia Muslim. Additional examples, may be based on race or creed, or a subgroup within a group, such as nationality (e.g., Icelandic), or such as sect within a religious group (e.g., Hasidic Jews).

In one embodiment, a method is provided to determine the relevance of copy number variant in a subject comprising comparing information of one or more copy number variants from the genome of a subject to a compilation of data of the frequencies of copy number variants in at least 100 subjects, and determining the relevance of said one or more copy number variants from the comparison in the preceding step. In another embodiment, the compilation comprises data from at least 100, 1000, 5000, 10,000, 25,000 or 50,000 subjects. In a preferred embodiment the data represents genome-wide analysis. In another embodiment, the data provides frequencies of occurrence for one or more copy number variants in said compilations from at least 100, 1000, 5000, 10,000, 25,000 or 50,000 subjects.

In one aspect, the KMTs of the present invention allow for a determination of whether one or more copy number variation in a subject, test subject or patient is associated with a condition or disease. In another aspect, the KMTs of the present invention allow for a determination of whether to eliminate or utilize a particular therapeutic in a subject, based on the information provided of one or more copy number variants in a subject.

In one embodiment, array comparative genome hybridization is utilized to obtain information of one or more copy number variations in each subject.

In one aspect the data compilations in one or more databases provide information comprising information of breakpoint maps for the subjects. In one embodiment, PCR screening is utilized to obtain information about one or more copy number variants.

One aspect of the invention is directed to accessing as set of data representing frequencies of one or more copy number variants in at least 100, 1000, 5000, 10,000, 25,000 or 50,000 subjects. In one embodiment, such involves computer executable logic, computer peripherals and computer hardware.

Another aspect of the invention provides a computer executable logic comprising a computer readable medium for enabling a processor to determine the relevance of one or more copy number variants in the genome of a subject. The computer executable logic comprises the processor receiving a set of data comprising frequency data for one or more copy number variants from the genome of at least 100, 1000, 5,000, 10,000, 25,000 or 50,000 subjects. In another embodiment, the comparison is to one or more data sets comprising one or more cohorts wherein each cohort represents an ethnic group and wherein the frequencies of one or more copy number variants are comprised in data sets for each of one or more cohorts.

In one embodiment one or more data sets of the invention comprise frequency data for one or more cohorts, wherein each cohort represents an ethnic groups, and wherein each data set is a compilation of data obtained from at least 100, 1000, 5000, 10,000, 25,000 or 50,000 subjects. The computer executable logic further directs the processor to compare copy number variations from a subject, test subject or patient, to the preceding one or more data sets. In addition, the computer executable logic further directs the processor to provide output in an electronic or paper format which determines the significance of one or more copy number variants present in said subject, test subject, or patient, relative to a phenotype associated with a disease, condition or disorder. In another embodiment, the determination is whether a particular therapeutic should be eliminated, initiated or used in combination with another therapeutic, in designing a therapeutic regimen for said subject, test subject or patient.

In one embodiment the data comprising the copy number variants for one or more cohorts, or for a subject, test subject or patient, is obtained through comparative genome wide comparative hybridization analysis or breakpoint mapping analysis. In one embodiment the data is obtained through array comparative genome hybridization. In another embodiment, the breakpoint mapping analysis is conducted by PCR.

In another aspect of the invention, a method is directed to identifying a therapeutic useful for treating a condition comprising obtaining information from the genome of a cohort of subjects undergoing clinical trial for said condition, wherein the method comprises identifying one or more copy number variant in said cohort, comparing said one or more variant to a data compilation corresponding to frequencies of copy number variants in at least 100, 1000, 5,000, 10,000, 25,000 or 50,0000 subjects to determine whether said one or more copy number abnormalities in said cohorts are present in said 100, 1000, 5,000, 10,000, 25,000 or 50,000 subjects, thus correlating the relevance of said one or more copy number abnormalities in said cohort to said condition, and identifying whether said therapeutic is useful for treating said condition.

In one embodiment, by comparison of copy number variants in a subject to a data set for a particular cohort, the method is directed to identification of one or more subpopulations from said cohort in which said therapeutic is useful in treatment, where the therapeutic is identified as useful, if the benefits outweigh any adverse effects or the therapeutic is identified as not useful if the adverse effects outweigh any benefits. In a preferred embodiment, the KMTs incorporating copy number variant data sets for a cohort or a subgroup(s) within a cohort are compared to copy number variants in a patient provide copy number variant frequencies that allow a determination for whether one or more copy number variants in subgroup(s) of said cohort are identified for whom said drug should be prescribed (i.e., is useful in therapy) or should not be prescribed (i.e., drug adverse effects outweigh any benefits).

Another embodiment of the invention includes business methods of commercializing and licensing the KMTs, creating a CLIA lab for performing the genomic screening or assays for significant biomarkers identified with the KMTs, and forming licensing agreements with other institutions or groups for researching and gathering additional genomic information for inclusion in and expansion of the KMTs.

Another aspect of the invention is directed to a business method where evaluation of copy number variant(s) identified in a subject or subgroup or cohort is provided to an individual or group, where the method comprises providing a computer executable logic directing a processor to determine the relevance of said copy number variant(s), where said variants are input as data through an automatic or manual process, whereby the processor receives said input data, where said processor compares said input data to a data set representing copy number variant frequencies present in at least 100, 1000, 5000, 10,000, 25,000 or 50,000 subjects, to determine the significance of input data relative to a phenotype associated with a condition, disease or disorder.

DEFINITIONS

Figure 1:
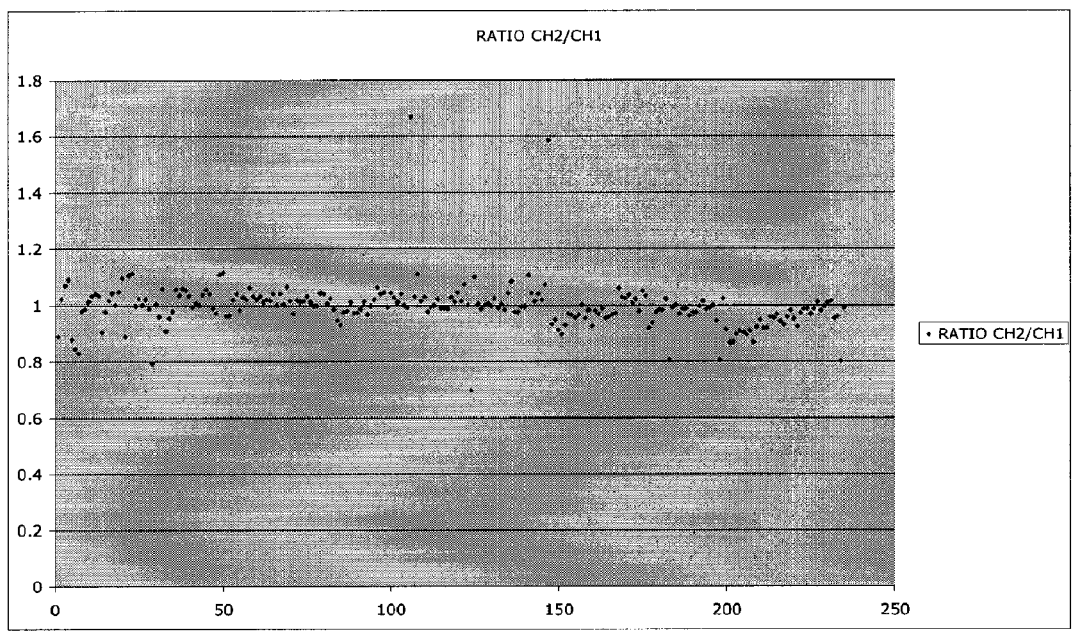
FIG. 1 depicts a graph corresponding to a chip array analysis via normal variants provided by the present invention's KMTs, resulting in identification of three medically relevant biomarkers; more specifically, two markers occur near 1.6 (Y axis) and one occurs near 0.6 (Y axis).

Array—General term referring to an orderly arrangement of elements, to each of which has been assigned an address and an ID. In molecular biology, the term "array" is typically used to refer to arrangements of DNA, RNA, proteins, oligonucleotides, aptamers, or tissues.

Array-Based Comparative Genomic Hybridization (aCGH)—The use of arrays for the simultaneous interrogation of thousands/millions of DNA sequences, whose genomic location is known. Comparison is between a 'control' and a test sample. aCGH is not limited to any particular array platform but is often considered synonymous with genomic arrays based on the use of bacterial artificial chromosomes (BACs-BAC arrays). In one nonexclusive meaning, aCGH is different from the majority of array analysis performed, namely that based on the comparison between expressions of genes in different tissues/individuals. The use of genomic DNA in aCGH results in data that has a simplistic structure, as each genomic segment may only be present in a discrete number of copies (usually 0, 1, 2, 3 or 4), whereas the expression levels of genes may vary from close to 0 to many million-fold.

Bacterial Artificial Chromosomes (BACs)—The mainstay of the human genome sequencing project, BACs are vectors that allow for the isolation of genomic DNA segments of approximately 150,000 bp in size. The public project was based on the sequencing of the complete inserts of BACs, at high redundancy. DNA obtained from BACs whose genomic address is known, can be used to synthesize BAC arrays, whose performance in the detection of copy number abnormalities is highly robust. Moreover, BACs reporting a variant may immediately be queried on publicly available databases in order to obtain genomic location and gene content information.

Breakpoint Mapping—The characterization of the precise molecular boundaries of any translocation/deletion/duplication/inversion. The information obtained from the molecular analysis of a given lesion (deletion, for example) allows for the creation of a simplified assay for detection of that lesion. In one nonexclusive example, the molecular boundaries of a common microdeletion at a particular loci is isolated and the information used to generate a simple PCR-based assay that is capable of interrogating the genomes of individuals very rapidly.

Copy Number Analysis—Detection of the number of copies of a given genomic segment by interrogation of whole genomes in a single experiment. In the human genome, this is of relevance to the creation of normal variation Knowledge Management Tools, and also of ascertaining correlations between certain disease states and the presence of dosage imbalances. Examples include a decrease in copy number from 2 to 1 in the case of a heterozygous deletion and an increase from 2 to 3 in the case of a heterozygous duplication.

Dosage Polymorphism—Copy number polymorphism. The presence in the population of a genomic variant defined by an abnormal copy number (the normal copy number is 2 for most chromosomes). Formally, a polymorphism includes occurrences in at least 1% of the population but this definition has been relaxed in the case of human genomic/genetic variation so that variants that are believed to be 'benign' but which still occur less often than 1% are still termed polymorphisms. A more accurate term is 'variant', as this does not imply a given minimum frequency.

Fluorescence In Situ Hybridization (FISH)—A method for visualizing a given sequence in the context of chromosomal position. Briefly, DNA is labeled with fluorescent dyes and hybridized to a set of immobilized chromosomes from the individual of interest. Each sequence is detected as localized fluorescence at the relevant genomic location. Useful for detecting/validating suspected copy number changes (e.g., in a heterozygous deletion, a spot will be seen on only one of the two chromosome homologues).

Haplotype—A set of closely linked alleles (genes/DNA polymorphisms/SNPs) inherited as a unit. It is not trivial to deduce a haplotype from genotype information, which usually reports nothing about which chromosome a given variant is on. For example, if an individual is Aa at a given locus and Bb at another, the relevant haplotypes could either be AB/ab or Ab/Ba.

Karyotype—A description of the content and structure of the chromosomes in a given cell type. This analysis, which relies on direct light microscope visualization of the chromosomes, has been the mainstay of 'whole-genome' analysis in the past 50 years but suffers from a lack of resolution, in that changes of 10-20 MB are required before an variant is detected. While likely to be superseded at many levels by aCGH, karyotyping will still be necessary to detect translocations, which may be copy number neutral and, therefore, not detectable by aCGH.

Single Nucleotide Polymorphism (SNP)—The most basic unit of variation at the level of DNA sequence. SNP includes variants in the nature of a single base—for example, at a given position, some individuals may have a 'G', while others may have a 'C'. Many of these changes are considered neutral while others may affect predisposition to certain disease states. Many 'SNPs are present in far less than 1% of the population. Another meaning includes a single nucleotide variant.

Subject—The term "subject" can mean a subject from whom genomic DNA is obtained for genome analysis by one or more methods described herein so as to obtain copy number variant data. Thus, a subject can be one individual from at least 100, 1000, 5000, 10,000, 25,000 or 50,000 individuals utilized to compile said data (or data set) for one or more cohorts, wherein a cohort represents an ethnic group, a patient group, a patient group associated with a particular condition, disease or disorder, a group of subgroup of individuals associated with a particular response to a treatment regimen, or clinical trial. In addition, a subject can mean a test subject, a patient or a candidate for a therapeutic, where genomic DNA from said subject, patient, or candidate is obtained for genome analysis by one or more methods of the present invention herein, so as to obtain copy number variant data in said subject, patient or candidate.

Drug Rescue—The term "rescue" or "drug rescue" as used herein means identification of individual genetic variations, which may explain the differences in the response of subjects to drugs in clinical trials. In addition, some drugs show unexpected toxicity after several months on the market. These rare adverse events, not previously reported in the pre-marketing trials, can jeopardize the drug's success and decrease its market share. The present invention's KMTs platform allows a clinician or medical professional to quickly examine copy number variants in a particular patient and determine whether such variants are associated with variants occurring in copy number of genes associated with the drug's pathway and search for the genetic variations associated with the particular adverse events. Thus, "rescue" or "drug rescue" involves identification of which copy number variations cause differences in drug response. This information is then used to define a subset of the population for which the drug should not be prescribed and a screening test identifying these patients is developed. This information can also be used to redefine the lead compound, allowing for a better understanding of its potential effects. Therefore, the KMTs provide pharmacogenomics platforms comprising optimized and automatic data mining capabilities, high throughput genotyping, statistical and bioinformatics analysis, and target validation.

DETAILED DESCRIPTION OF THE INVENTION

In one aspect, the present invention provides a knowledge management tool (KMT) for cytogeneticists to rationally interpret genomic data, including array CGH (aCGH) data in patients. In addition to yielding highly relevant information about copy number variation in the general population, the KMT will also yield insights into the underlying etiologies in a broad range of disorders and diseases. Genome wide copy number detection, as described in this application, is the most robust and efficient platform for screening genomes for variation, both normal and associated with disease. In one embodiment, the use of the KMT permits improved accuracy for diagnosing patients through the genetic evaluations conducted in cytogenetic and reference diagnostic labs. This tool allows a comparison of results against a compilation of genetic information derived from thousands of individuals to focus the analysis and permit one to distinguish between diseases and/or conditions and disregard normal variations in the genome. In one embodiment, there is predictive or personalized medicine resulting from an analysis of the patient's genome.

This analysis provides a snapshot of the normal and abnormal copy number variations coupled with a linkage to pharmaceuticals and treatments targeted to an individual's genetic profile. In particular, one embodiment permits the identification of those patients who can be treated effectively with a pharmaceutical or those who might have an adverse side-effect from a particular drug. This stratification based on copy number variations is particularly useful to focus treatment into the short window that may produce results and reduce any detours or damaging treatments.

In one embodiment, the information on normal variations and the KMT is used in providing diagnostic assays for medically relevant biomarkers and assisting in the development and research efforts for additional markers. Another embodiment provides "translational medicine" to accelerate research discoveries to patients as quickly as possible. This includes a CLIA lab performing diagnostic evaluations of the copy number variations utilizing both microarray based and non-microarray based analyses.

In one aspect of the invention, a database of copy number variants comprises an major feature of the KMTs of the present invention. In one embodiment, the database provides information on copy number variant frequencies from 10,000 individuals (e.g., normals, not displaying a targeted/identified phenotypic effect). Previous studies have shown, for example, that the frequency of 47,XXY was 1:1,000. Thus, there were only 10 such individuals ascertained in the cohort of 10,000 newborns. As such, a database of only 1,000 individuals would have resulted in a significant possibility that this well-known and important chromosome abnormality would either not have been detected or detected only once. In another embodiment, the database will provide such information for all subgroups of a population (e.g., ethnic groups in the human population), where designated subgroups can be based on ethnicity, geography, race, or any other identifiable population group or subgroup.

The following sample calculation that illustrates how an interpretation of the significance of a copy number change in a disease state would proceed:

A given copy number variant is present in a proportion, p<1, of individuals with a given phenotype. A comparison of that figure to the KMT, shows that none in the normal cohort possess this change. What follows is a statistical analysis for different values of (p) and the database size, (n):

TABLE 1

| Proportion p | Database size n | Likelihood of no variants in KMT* |
|---|---|---|
| 0.001 | 100 | 0.904792147 |
| 0.001 | 500 | 0.606378945 |
| 0.001 | 1000 | 0.367695425 |
| 0.001 | 5000 | 0.006721112 |
| 0.001 | 10000 | 4.51733E−05 |
| 0.01 | 100 | 0.366032341 |
| 0.01 | 500 | 0.006570483 |
| 0.01 | 1000 | 4.31712E−05 |
| 0.01 | 5000 | 1.49959E−22 |
| 0.01 | 10000 | 2.24877E−44 |
| 0.1 | 100 | 2.65614E−05 |
| 0.1 | 500 | 1.32207E−23 |
| 0.1 | 1000 | 1.74787E−46 |
| 0.1 | 5000 | 1.6314E−229 |
| 0.1 | 10000 | 0 |
| 0.2 | 100 | 2.03704E−10 |
| 0.2 | 500 | 3.50747E−49 |
| 0.2 | 1000 | 1.23023E−97 |
| 0.2 | 5000 | 0 |
| 0.2 | 10000 | 0 |
| 0.5 | 100 | 7.88861E−31 |
| 0.5 | 500 | 3.0549E−151 |
| 0.5 | 1000 | 9.3326E−302 |
| 0.5 | 5000 | 0 |
| 0.5 | 10000 | 0 |

*= $(1-p)^n$

As the non-limiting example above demonstrates, where the frequency of the copy number change in a disease cohort is 0.001 (1/1,000), a database of at least 5,000 is sufficient to identify whether the variation is "normal" or linked to disease. As the size of a database is reduced, the likelihood that the copy number change is not present is high (i.e., for a size of 100, it is over 0.9 etc). Of course, this is but one example, and depending on the frequency of one or more variants the required number of individuals in a given database becomes correspondingly smaller.

In other words, for variants present at higher levels in the disease group, the statistics become significant in databases of smaller sizes. Therefore, where a given gene or gene region is implicated in a given disorder, while every individual affected by that disease may have some abnormality of that gene, a copy number change is present only in a small minority. Hence, the confidence level is important for copy number change in disease cohorts, even where they are rare in that group. For example, there is no debate about the importance of the APP gene in Alzheimer etiology. However, only a small proportion (~8% at the very most) have a copy number change (recently described duplication). This finding, however, has dramatic significance if it can be shown that virtually no normal individuals have such a variant. Of course, a large database exceeding the required confidence level for a subject or cohort of subjects will necessarily meet the confidence level requirement for databases requiring a smaller number of individuals.

Another embodiment includes a variety of products for evaluating the copy number. These include the normal copy number variation KMT, the copy number breakpoint KMT, CGH arrays for screening the genome and genome probes tailored to interrogate the genome Additional products are specifically focused PCR-based assay kits for the detection of microdeletions/microduplications.

In yet another aspect of the present invention, PCR assays are utilized and provide an alternative to array analysis. In particular, the PCR assays detect precise boundaries of gene/chromosome variants, at the molecular level, which boundaries are identical in different individuals. For example, the molecular boundaries of a microdeletion on chromosome 8 (present in 5% of all normal individuals) was sequenced in 100 individuals and is shown to have an identical sequence across the breakpoint. A feature of this aspect of the invention is that a deletion(s) is detected, not by array analysis, but by the use of a simple PCR assay. This assay is based on the amplification of a junction fragment present only in individuals that carry this deletion. (e.g., FIG. 2). This assay converts the detection of a loss by array CGH to one of a gain by PCR.

Different DNA isolation and PCR techniques are well known in the art. Examples of PCR techniques that can be used in the present invention include, but are not limited to quantitative PCR, quantitative fluorescent PCR (QF-PCR), multiplex fluorescent PCR (MF-PCR), real time PCR (RT-PCR), single cell PCR, PCR-RFLP/RT-PCR-RFLP, hot start PCR and Nested PCR. Other suitable amplification methods include the ligase chain reaction (LCR), ligation mediated PCR (LM-PCR), degenerate oligonucleotide probe PCR (DOP-PCR), transcription amplification, self-sustained sequence replication, selective amplification of target polynucleotide sequences, consensus sequence primed polymerase chain reaction (CP-PCR), arbitrarily primed polymerase chain reaction (AP-PCR) and nucleic acid based sequence amplification (NABSA).

PCR can be conducted using methods and reagents known in the art. For example, the PCR products can be directly sequenced bi-directionally by dye-terminator sequencing. PCR is performed in a 384-well plate in a volume of 15 ul containing 5 ng genomic DNA, 2 mM MgCl2, 0.75 ul DMSO, 1 M Betaine, 0.2 mM dNTPs, 20 pmol primers, 0.2 ul Ampli-Taq Gold (Applied Biosystems), 1× buffer (supplied with AmpliTaq Gold). Thermal cycling conditions are as follows: 95° C. for 10 minutes; 95° C. for 30 seconds, 60° C. for 30 seconds, 72° C. for 1 minute for 30 cycles; and 72° C. for 10 minutes. PCR products are purified with Ampure® Magnetic Beads (Agencourt) and optionally can be separated by capillary electrophoresis on an ABI13730 DNA Analyzer (Applied Biosystems).

In one embodiment, a PCR-based approach is real-time quantitative PCR (qPCR). Alternative methods for the simultaneous interrogation of multiple regions include quantitative multiplex PCR of short fluorescent fragments (QMPSF), multiplex amplifiable probe hybridization (MAPH) and multiplex ligation-dependent probe amplification (MLPA), in which copy-number differences for up to 40 regions can be scored in one experiment. Another approach is to specifically target regions that harbour known segmental duplications, which are often sites of copy-number variation. By targeting the variable nucleotides between two copies of a segmental duplication (called paralogous sequence variants) using a SNP-genotyping method that provides independent fluorescence intensities for the two alleles, it is possible to detect an increase in intensity of one allele compared with the other.

In another embodiment, the amplicons are bound to beads using the sequencing element of the nucleic acid tag under conditions that favor a single amplicon molecule to bind a different bead and amplification occurs on each bead. In some embodiments, such amplification occurs by PCR. Each bead can be placed in a separate well, which can be a (optionally addressable) picolitre-sized well. In some embodiments, each bead is captured within a droplet of a PCR-reaction-mixture-in-oil-emulsion and PCR amplification occurs within each droplet. The amplification on the bead results in each bead carrying at least one million, at least 5 million, or at least 10 million copies of the single amplicon molecule.

In embodiments where PCR occurs in oil-emulsion mixtures, the emulsion droplets are broken, the DNA is denatured and the beads carrying single-stranded nucleic acids clones are deposited into a well, preferably a picolitre-sized well, for further analysis according to the methods described herein. These amplification methods allow for the analysis of genomic DNA regions. Methods for using bead amplification followed by fiber optics detection are described in Margulies et al. 2005, Nature. 15; 437(7057):376-80, and as well as in US Publication Application Nos. 20020012930; 20030068629; 20030100102; 20030148344; 20040248161; 20050079510, 20050124022; and 20060078909.

In certain aspects of the invention, nucleic acid molecules (e.g., genomic DNA) are sequenced utilizing sequencing methods that are conventional in the art. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in substantially real time or real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read.

In some embodiments, high-throughput sequencing involves the use of technology available by Helicos Bio-Sciences Corporation (Cambridge, Mass.) such as the Single Molecule Sequencing by Synthesis (SMSS) method. SMSS is unique because it allows for sequencing the entire human genome in up to 24 hours. This fast sequencing method also allows for detection of a SNP/nucleotide in a sequence in substantially real time or real time. Finally, SMSS is powerful because, like the MIP technology, it does not require a preamplification step prior to hybridization. In fact, SMSS does not require any amplification. SMSS is described in US Publication Application Nos. 20060024711; 20060024678; 20060012793; 20060012784; and 20050100932. In some embodiments, high-throughput sequencing involves the use of technology available by 454 Lifesciences, Inc. (Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

In some embodiments, PCR-amplified single-strand nucleic acid is hybridized to a primer and incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process repeats until the entire sequence is determined. In one embodiment, pyrosequencing is utilized to analyze amplicons to determine whether breakpoints are present. In another embodiment, pyrosequencing also maps surrounding sequences as an internal quality control.

Pyrosequencing analysis methods are known in the art. Sequence analysis may include a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structured such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer:nonamer complexes are stripped and a new cycle begins. Methods to image sequence information after performing ligation are known in the art.

In another aspect, whole genome-based array CGH analysis can be used to efficiently interrogate human genomes for genomic imbalances at multiple loci within a single assay. The importance of normal copy-number variation involving large segments of DNA has been unappreciated, until now. Array CGH is a breakthrough technique in human genetics, which is attracting interest from clinicians working in fields as diverse as cancer and IVF (In Vitro Fertilization). The use of CGH microarrays in the clinic holds great promise for identifying regions of genomic imbalance associated with disease. Advances from identifying chromosomal critical regions associated with specific phenotypes to identifying the specific dosage sensitive genes will lead to therapeutic opportunities of benefit to patients. Array CGH is a specific, sensitive and rapid technique that enables the screening of the whole genome in a single test. It will facilitate and accelerate the diagnostic process in human genetics and is expected to have a profound impact on the screening and counseling of patients with genetic disorders. It is now possible to identify the exact location on the chromosome where an aberration has occurred and it is possible to map these changes directly onto the genomic sequence.

An array-based comparative genome hybridization (array-CGH) approach provides one of the most robust methods for carrying out genome-wide scans to find novel copy number variants (CNVs). These approaches use labeled fragments from a genome of interest, which are competitively hybridized with a second differentially labeled genome to arrays that are spotted with cloned DNA fragments, revealing copy-number differences between the two genomes. Genomic clones (for example, BACs), cDNAs, PCR products and oligonucleotides can all be used as array targets. The use of array-CGH with BACs is particularly popular, owing to the extensive coverage of the genome it provides, the availability of reliable mapping data and ready access to clones. The last of these factors is important both for the array experiments themselves, and for confirmatory FISH experiments.

The use of CGH with arrays that comprise long oligonucleotides (60-100 bp) can improve the detection resolution over that achieved using BACs (which starts from 50 kb to, theoretically, a few kb), and was first implemented in an assay format that is known as representational oligonucleotide microarray analysis (ROMA). The principle of ROMA is similar to that applied in the use of BAC arrays, but to increase the signal-to-noise ratio, the 'complexity' of the input DNA is reduced by a method called representation or whole-genome sampling. Here the DNA that is to be hybridized to the array is treated by restriction digestion and then ligated to adapters, which results in the PCR-based amplification of fragments in a specific size-range. As a result, the amplified DNA makes up a fraction of the entire genomic sequence—that is, it is a representation of the input DNA that has significantly reduced complexity, which leads to a reduction in background noise. Companies such as NimbleGen and Agilent Technologies have developed other long-oligonucleotide arrays that can be used for direct (non-representational) CGH. The resolution of most available oligonucleotide arrays is in the 30 to 50-kb range, which will increase as higher-resolution arrays become available.

Another variation on the array-based approach is to use the hybridization signal intensities that are obtained from spotted oligonucleotides on Affymetrix SNP arrays. Here hybridization intensities are compared with average values that are derived from controls, such that deviations from these averages indicate a change in copy number. As well as providing information about copy number, SNP arrays have the added advantage of providing genotype information. For example, they can reveal loss of heterozygosity, which could provide supporting evidence for the presence of a deletion, or might indicate segmental uniparental disomy (which can also be considered as a form of structural variation).

Chromosome banding is one of the most widely used techniques in routine cytogenetics and has been invaluable in the search for chromosomal aberrations causally related to e.g. mental retardation and congenital malformation syndromes. Conceptual and technical developments in molecular cytogenetics are now enhancing the resolving power of conventional chromosome analysis techniques from the megabase to the kilobase level. Tools that have mediated these developments include (a) the generation of genome-wide clone resources integrated into the finished human genome sequence, (b) the development of high-throughput microarray platforms, and (c) the optimization of comparative genomic hybridization protocols and data analysis systems. Together, these developments have accumulated in a so-called "molecular karyotyping" technology that allows the sensitive and specific detection of single copy number changes of submicroscopic chromosomal regions throughout the entire human genome.

Many of the basic procedures followed in microarray-based genome profiling are similar, if not identical, to those followed in expression profiling and SNP analysis, including the use of specialized microarray equipment and data-analysis tools. Since microarray-based expression profiling has been well established in the last decade, much can be learned from the technical advances made in this area. Examples of the use of microarrays in nucleic acid analysis that may be used are described in U.S. Pat. No. 6,300,063, U.S. Pat. No. 5,837,832, U.S. Pat. No. 6,969,589, U.S. Pat. No. 6,040,138, U.S. Pat. No. 6,858,412, U.S. application Ser. No. 08/529, 115, U.S. application Ser. No. 10/272,384, U.S. application Ser. No. 10/045,575, U.S. application Ser. No. 10/264,571 and U.S. application Ser. No. 10/264,574. It should be noted that there are also distinct differences such as target and probe complexity, stability of DNA over RNA, the presence of repetitive DNA and the need to identify single copy number alterations in genome profiling.

Sub-microscopic copy number alterations do not always have phenotypic consequences, as in some cases identical alterations were found in either one of the normal parents. This notion has been substantiated by recent studies revealing the presence of LCVs (large copy number variations) in apparently normal individuals. In addition, once it has been established that a copy number alteration has occurred in a patient, it may be that this alteration has not been described before in the literature, posing serious problems for genetic counseling. However, in due time increasing numbers of these abnormalities will continue to be documented, either in individual case reports or in publicly available online databases, furthering our understanding of the genetic basis of these disorders. The KMTs of this invention provide a compilation of information on normal copy number variations to permit an identification and analysis of those variations of significance.

The development of comparative genomic hybridization (CGH) (Kallioniemi et al, 1992, Science 258: 818-21) provided the first efficient approach to scanning entire genomes for variations in DNA copy number. In a typical CGH measurement, total genomic DNA is isolated from test and reference cell populations, differentially labeled, and hybridized to a representation of the genome that allows the binding of sequences at different genomic locations to be distinguished. More than two genomes can be compared simultaneously with suitable labels. Hybridization of highly repetitive sequences is typically suppressed by the inclusion of unlabeled Cot-1 DNA in the reaction. Originally, metaphase chromosomes were used for the representation of the genome and the location of copy number variations between test and reference genomic DNA was mapped to the physical position on the chromosomes.

Now chromosomes have largely been replaced by DNA microarrays containing elements that are mapped directly to the genome sequence (Pinkel et al, 1998. Nat. Genet. 20:207-11). The relative hybridization intensity of the test and reference signals at a given location is then (ideally) proportional to the relative copy number of those sequences in the test and reference genomes. If the reference genome is normal then increases and decreases in signal intensity ratios directly indicate DNA copy number variation within the genome of the test cells. Data are typically normalized so that the modal ratio for the genome is set to some standard value, typically 1.0 on a linear scale or 0.0 on a logarithmic scale. Additional measurements such as fluorescent in situ hybridization (FISH) or flow cytometry (Mohapatra et al, Genes Chromosomes Cancer, 20: 311-19) can be used to determine the actual copy number associated with a ratio level.

Array CGH has been implemented using a wide variety of techniques. The initial approaches used arrays produced from large-insert genomic clones such as bacterial artificial chromosomes (BACs). Producing sufficient BAC DNA of adequate purity to make arrays is arduous, so several techniques to amplify small amounts of starting material have been employed. These techniques include ligation-mediated polymerase chain reaction (PCR) (Snijders et al, Nat. Genet. 29:263-64), degenerate primer PCR using one or several sets of primers, and rolling circle amplification. BAC arrays that provide complete genome tiling paths are also available. Arrays made from less complex nucleic acids such as cDNAs, selected PCR products, and oligonucleotides can also be used. Although most CGH procedures employ hybridization with total genomic DNA, it is possible to use reduced complexity representations of the genome produced by PCR techniques. Computational analysis of the genome sequence can be used to design array elements complementary to the sequences contained in the representation. Various single nucleotide polymorphism (SNP) genotyping platforms, some of which use reduced complexity genomic representations, are useful for their ability to determine both DNA copy number and allelic content across the genome.

The different basic approaches to array CGH provide different levels of performance, so some are more suitable for particular applications than others. The factors that determine the performance requirements include the magnitudes of the copy number changes, their genomic extents, the state and composition of the specimen, how much material is available for analysis, and how the results of the analysis will be used. Many applications require reliable detection of copy number changes of much less than 50%, a more stringent requirement than for other microarray technologies. Note that technical details are extremely important and different implementations of the "same" array CGH approach may yield different levels of performance. Various CGH methods are known in the art and are equally applicable to one or more methods of the present invention. For example, CGH methods are disclosed in U.S. Pat. Nos. 7,034,144; 7,030,231; 7,011,949; 7,014,997; 6,977,148; 6,951,761; and 6,916,621, the disclosure from each of which is incorporated by reference herein in its entirety.

The data provided by array-CGH (aCGH) are quantitative measures of DNA sequence dosage. Array-CGH provides high-resolution estimates of copy number aberrations, and can be performed efficiently on many samples. The advent of array-CGH technology makes it possible to monitor DNA copy number changes on a genomic scale and many projects have been launched for studying the genome in specific diseases. For example, chromosomal aberrations play a pivotal role in cancer progression, where knowledge of genomic instability promises to lead to improved cancer diagnostics and treatments.

The mechanism of cancer progression involves chromosomal aberrations, including amplification of oncogenes and deletion of tumor suppressor genes. These chromosomal aberrations are best revealed via array-CGH analysis. As the effective resolution of array CGH techniques increases, an increasing rate of discovery of medically important dosage aberrations will result. However, interpreting the primary data becomes more complex due to the need to better understand normal polymorphisms, both in the germline and tumor genome. The further elucidation of dosage polymorphisms remained experimental rather than a computational endeavor without high quality aCGH data available on a very large number of normal individuals. Understanding those dosage polymorphisms that are detectable by array CGH is important so that normal variations are not falsely associated with disease, and conversely to determine if some so-called normal variations may underlie certain disease susceptibilities. The normal variation KMT fills this void.

Copy number abnormalities currently represent a significant untapped opportunity in the field of predictive medicine. Personalized medicine is a component of the molecular diagnostics market, which is the fastest growing segment of the in vitro diagnostics market. According to S. G. Cowen and Co., the IVD was a $26 Billion industry in 2004. Within this industry, the molecular diagnostics market segment is expected to show the most robust growth, increasing from $1.8 Billion in 2004 to $3.6 Billion in 2009, representing an annual growth rate of 15%.

Specifically, the array CGH procedure includes the following steps. First, large-insert clones such as BACs are obtained from a supplier of clone libraries. Then, small amounts of clone DNA are amplified by either degenerate oligonucleotide-primed (DOP) PCR or ligation-mediated PCR in order to obtain sufficient quantities needed for spotting.

Next, these PCR products are spotted onto glass slides using microarray robots equipped with high-precision printing pins. Depending on the number of clones to be spotted and the space available on the microarray slide, clones can either be spotted once per array or in replicate. Repeated spotting of the same clone on an array increases precision of the measurements if the spot intensities are averaged, and allows for a detailed statistical analysis of the quality of the experiments.

Subject and control DNAs are usually labeled with either Cy3 or Cy5-dUTP using random priming and are subsequently hybridized onto the microarray in a solution containing an excess of Cot1-DNA to block repetitive sequences. Hybridizations can either be performed manually under a coverslip, in a gasket with gentle rocking or, automatically using commercially available hybridization stations. These automated hybridization stations allow for an active hybridization process, thereby improving the reproducibility as well as reducing the actual hybridization time, which increases throughput.

The hybridized DNAs are detected through the two different fluorochromes using standard microarray scanning equipment with either a scanning confocal laser or a charge coupled device (CCD) camera-based reader, followed by spot identification using commercially or freely available software packages. Any conventional fluorochrome can be utilized in the invention. These are well known and commercially available. Specific examples of detectable molecules include radioactive isotopes such as $p^{32}$ or $H^3$, fluorophores such as fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, $I^2$-galactosidase, and hapten conjugates such as digoxigenin or dinitrophenyl, etc. Other detectable markers include chemiluminescent and chromogenic molecules, optical or electron density markers, etc. The probes can also be labeled with semiconductor nanocrystals such as quantum dots (i.e., Qdots), described in U.S. Pat. No. 6,207,392. Qdots are commercially available from Quantum Dot Corporation.

Additional examples of reagents which are useful for detection include, but are not limited to, radiolabeled probes, fluorophore-labeled probes, quantum dot-labeled probes, chromophore-labeled probes, enzyme-labeled probes, affinity ligand-labeled probes, electromagnetic spin labeled probes, heavy atom labeled probes, probes labeled with nanoparticle light scattering labels or other nanoparticles or spherical shells, and probes labeled with any other signal generating label known to those of skill in the art. Non-limiting examples of label moieties useful for detection in the invention include, without limitation, suitable enzymes such as horseradish peroxidase, alkaline phosphatase, β-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue™, Texas Red, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6$^{th}$ Edition of the Molecular Probes Handbook by Richard P. Hoagland; a luminescent material such as luminol; light scattering or plasmon resonant materials such as gold or silver particles or quantum dots; or radioactive material include $^{14}C$, $^{123}I$, $^{124}I$, $^{125}I$, $^{131}I$, Tc99m, $^{35}S$ or $^3H$.

Examples of labels include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Genotyping using a microarray can be performed using any of a variety of methods, means and variations thereof for carrying out array-genotyping analysis.

Furthermore, backbone labels are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

The increase in data obtained through high-density arrays requires standardized storage systems as well as thorough statistical tools, similar to those required for microarray-based gene expression profiling. Owing to the complicated process of producing and hybridizing spotted microarrays, a certain degree of systematic variation does exist in the data produced.

Normalization of microarray data is used to eliminate such systematic variation and, therefore, represents an important preprocessing step in the analysis of almost all microarray data. After data normalization, automated statistical procedures are required for reliable detection of genomic copy number changes. Finally, digitized intensity differences in the hybridization patterns of the DNAs onto the cloned fragments can be interpreted as copy number differences between the test and reference genomes. This technique, once established and validated, allows high-throughput DNA copy number screening with a resolution limited only by the size of the clone fragments used (typically ~100 kb using BAC arrays).

The information included in the normal copy number variation KMT is obtained by screening the genome of a large population of individuals using conventional techniques of array CGH. The samples from these individuals for evaluation of the nucleic acid may include any conventional biological sample for obtaining the necessary genomic material. The samples may be cells, blood, bodily fluids, amniotic fluid, biopsies, or tissue. Furthermore, samples can be fresh, from cells/tissue in culture or from archival cells/tissue, such as frozen samples, Guthrie cards, cord blood, or placenta. Sampling in this context, includes conventional methods in the art of obtaining a blood sample or cell sample, including buccal, nasal or throat swabs. In addition, in one or more methods of the invention, the samples for genomic evaluation can be obtained from a newborn, child, pre-teen, teen or adult subject. In another embodiment, a sample is obtained via amniocentesis to provide a DNA sample for genomic analysis.

In one or more KMTs of the present invention, a reference database can be comprised of evaluations obtained from a ratio of male to female subjects. In one embodiment, the ratio is 1:1, or nearly 1:1 or about 1:1.

In another aspect, the samples are obtained from a child and the sample obtained is blood or a buccal sample. In another embodiment, the sample is obtained from a newborn, and the sample obtained is blood. In yet another embodiment, the sample is obtained from mixed subject pool where the subject is selected from a group consisting of a newborn, infant, a child, a pre-teen, teen, a young adult, a middle-aged adult and an older adult. For example, a database of normal copy number variants can be compiled from 10,000 individuals, wherein said individuals are comprised of newborns and young adults, or any combination of age cohorts desired.

The age (i.e., in days or years) for subjects from whom genomic evaluations comprise the KMTs of the present invention includes day 1 to day 40 (newborn), infant (age: 1 month to 1 year), 1 year to 8 years (child), 8 years to 12 (preteen years), 12 years to 19 years (teen), 19 years to 39 years (young adult), 39 years to 55 years (middle-aged), and 55 years to 100 years (older adult).

Moreover, obtaining genomic DNA from a subject is conventional in the art. Genomic DNA (gDNA) can be isolated from one or more cells, bodily fluids or tissues. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues such as buccal swab, mouthwash, surgical removal, biopsy aspiration or the like. Genomic DNA can also be obtained from one or more cell or tissue in primary culture, in a propagated cell line, a fixed archival sample, forensic sample or archeological sample.

Exemplary cell types from which gDNA can be obtained in a method of the invention include, without limitation, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which gDNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, or pluripotent stem cell.

A cell from which a gDNA sample is obtained for use in the invention can be a normal cell or a cell displaying one or more symptom of a particular disease or condition. Thus, a gDNA used in a method of the invention can be obtained from a cancer cell, neoplastic cell, necrotic cell or the like. Those skilled in the art will know or be able to readily determine methods for isolating gDNA from a cell, fluid or tissue using methods known in the art such as those described in Sambrook et al., Molecular Cloning: A Laboratory Manual, 3rd edition, Cold Spring Harbor Laboratory, New York (2001) or in Ausubel et al., Current Protocols in Molecular-Biology, John Wiley and Sons, Baltimore, Md. (1998).

A method of the invention can further include steps of isolating a particular type of cell or tissue. Exemplary methods that can be used in a method of the invention to isolate a particular cell from other cells in a population include, but are not limited to, Fluorescent Activated Cell Sorting (FACS) as described, for example, in Shapiro, Practical Flow Cytometry, 3rd edition Wiley-Liss; (1995), density gradient centrifugation, or manual separation using micromanipulation methods with microscope assistance. Exemplary cell separation devices that are useful in the invention include, without limitation, a Beckman JE-6 centrifugal elutriation system, Beckman Coulter EPICS ALTRA computer-controlled Flow Cytometer-cell sorter, Modular Flow Cytometer from Cytomation, Inc., Coulter counter and channelyzer system, density gradient apparatus, cytocentrifuge, Beckman J-6 centrifuge, EPICS V dual laser cell sorter, or EPICS PROFILE flow cytometer. A tissue or population of cells can also be removed by surgical techniques. For example, a tumor or cells from a tumor can be removed from a tissue by surgical methods, or conversely non-cancerous cells can be removed from the vicinity of a tumor. Using methods such as those set forth in further detail below, the invention can be used to compare typable loci for different cells including, for example, cancerous and non-cancerous cells isolated from the same individual or from different individuals.

A gDNA can be prepared for use in a method of the invention by lysing a cell that contains the DNA. Typically, a cell is lysed under conditions that substantially preserve the integrity of the cell's gDNA. In particular, exposure of a cell to alkaline pH can be used to lyse a cell in a method of the invention while causing relatively little damage to gDNA. Any of a variety of basic compounds can be used for lysis including, for example, potassium hydroxide, sodium hydroxide, and the like. Additionally, relatively undamaged gDNA can be obtained from a cell lysed by an enzyme that degrades the cell wall. Cells lacking a cell wall either naturally or due to enzymatic removal can also be lysed by exposure to osmotic stress. Other conditions that can be used to lyse a cell include exposure to detergents, mechanical disruption, sonication heat, pressure differential such as in a French press device, or Dounce homogenization. Agents that stabilize gDNA can be included in a cell lysate or isolated gDNA sample including, for example, nuclease inhibitors, chelating agents, salts buffers and the like. Methods for lysing a cell to obtain gDNA can be carried out under conditions known in the art as described, for example, in Sambrook et al., supra (2001) or in Ausubel et al., supra, (1998).

In particular embodiments of the invention, a crude cell lysate containing gDNA can be directly amplified or detected without further isolation of the gDNA. Alternatively, a gDNA can be further isolated from other cellular components prior to amplification or detection. Accordingly, a detection or amplification method of the invention can be carried out on purified or partially purified gDNA. Genomic DNA can be isolated using known methods including, for example, liquid phase extraction, precipitation, solid phase extraction, chromatography and the like. Such methods are often referred to as minipreps and are described for example in Sambrook et al., supra, (2001) or in Ausubel et al., supra, (1998) or available from various commercial vendors including, for example, Qiagen (Valencia, Calif.) or Promega (Madison, Wis.).

As used herein, the term "genomic DNA" or "gDNA" is intended to mean one or more chromosomal polymeric deoxyribonucleotide molecules occurring naturally in the nucleus of a eukaryotic cell or in a prokaryote, virus, mitochondrion or chloroplast and containing sequences that are naturally transcribed into RNA as well as sequences that are not naturally transcribed into RNA by the cell. A gDNA of a eukaryotic cell contains at least one centromere, two telomeres, one origin of replication, and one sequence that is not transcribed into RNA by the eukaryotic cell including, for example, an intron or transcription promoter. A eukaryotic genomic DNA can be distinguished from prokaryotic, viral or organellar genomic DNA, for example, according to the presence of introns in eukaryotic genomic DNA and absence of introns in the gDNA of the others.

In certain aspects, the genomic DNA can first be amplified. Accordingly, the term "amplified" is intended to mean a nucleic acid copy in which the proportion of each sequence in the copy relative to all other sequences in the copy is substantially the same as the proportions in the nucleic acid template. When used in reference to a population of genome fragments, for example, the term is intended to mean a population of genome fragments in which the proportion of each genome fragment to all other genome fragments in the population is substantially the same as the proportion of its sequence to the other genome fragment sequences in the genome. Substantial similarity between the proportion of sequences in an amplified representation and a template genomic DNA means that at least 60% of the loci in the representation are no more than 5 fold over-represented or under-represented. In such representations at least 70%, 80%, 90%, 95% or 99% of the loci can be, for example, no more than 5, 4, 3 or 2 fold over-represented or under-represented. A nucleic acid included in the term can be DNA, RNA or an analog thereof. The number of copies of each nucleic acid sequence in an amplified representative population can be, for example, at least 2, 5, 10, 25, 50, 100, 1000, $1\times10^4$, $1\times10^5$, $1\times10^6$, $1\times10^7$, $1\times10^8$ or $1\times10^{10}$ fold more than the template or more.

An advantage of the preceding amplification is that a small amount of genomic DNA can be obtained from an individual, and amplified to obtain an amplified representative population of genome fragments that can be interrogated in the methods of the invention. Thus, the methods are particularly useful for genotyping genomic DNA obtained from relatively small tissue samples such as a biopsy or archived sample. Generally, the methods will be used to amplify a relatively small number of template genome copies. In particular embodiments, a genomic DNA sample can be obtained from a single cell and genotyped.

The invention provides methods of whole genome amplification that can be used to amplify genomic DNA prior to genetic evaluation such as detection of typable loci in the genome. Whole genome amplification methods of the invention can be used to increase the quantity of genomic DNA without compromising the quality or the representation of any given sequence. Thus, the methods can be used to amplify a relatively small quantity of genomic DNA in a sequence independent fashion to provide levels of the genomic DNA that can be genotyped. Surprisingly, a complex genome can be amplified with a low processivity polymerase to obtain a population of genome fragments that is representative of the genome, has high complexity and contains fragments that have a convenient size for hybridization to a typical nucleic acid array.

Furthermore, amplification of genomic DNA in the methods disclosed herein does not require the polymerase chain reaction. Specifically, amplification can be carried out such that sequences are amplified several fold under isothermal conditions. Thus, although an elevated temperature step can be used, for example, to initially denature a genomic DNA template, temperature cycling need not be used. Accordingly, repeated increases in temperature, normally used to denature hybrids, and repeated return to hybridization temperatures need not be used.

For evaluating the copy number of subjects, any conventional biological sample may be utilized to obtain genomic DNA. The screening of the subject to identify copy number polymorphisms may be done using array CGH or conventional PCR techniques. The information about the copy number polymorphisms obtained through either of these methods may be compared against the KMTs for an evaluation of the significance of any variation found.

The technology of the invention features a portfolio of knowledge management tools of normal chromosomal variation in the human population. The rational interpretation of the significance of chromosomal aberrations in an individual cannot be made without reference to normal population variation. Diagnosticians, researchers and pharmaceutical developers who are relying on array CGH data all suffer from the same dilemma—the question of "what is normal".

One objective of this invention is the primary knowledge management tools (KMT) for cytogeneticists to rationally interpret array CGH data in patients. These tools are comprehensive genome-wide analysis tools for normal variation. In addition to yielding highly relevant information about copy number variation in the general population, this KMT also yields insights into the underlying etiologies in a broad range of disorders and diseases. The advantage of aCGH is that individuals can be studied on their own merits without having to rely on the statistical methods inherent in linkage association, wherein individuals with multiple genetic etiologies are likely to have been lumped together. The ultimate power of the array CGH based approach lies in the genome wide copy number assessment of patient samples without any a priori knowledge of the genomic regions involved.

In a an object of the invention, DNA samples are obtained from a subject to be analyzed to determine genome wide copy number variant, which analysis is conducted by one or methods described herein, whereby the output from such analysis is compared to a normal copy number variant database of the present invention, so as to determine if detected variations are associated with a phenotypic consequence. The subject can be of any age, gender, and ethnicity as described herein.

Genome wide copy number detection, as described in this invention, is the most robust and efficient platform for screening individuals to identify which variations are of significance for many different aspects. For example, this comparison permits the determination of variations associated with phenotypic consequences. It also allows the stratification of subjects within a population to distinguish between individuals based on their reaction to drugs, either good or adverse. This facilitates the segregation of a cohort of subjects responding to therapeutics in clinical trials from those not responding or experiencing adverse reactions so that the therapeutics may be rescued and targeted to subpopulations for whom the therapeutic is efficacious. Also, these KMTs can be utilized to follow drugs in use after regulatory approval, such as by the FDA, to continue monitoring the drug and its efficacy or adverse reaction within identified subpopulations of the group.

In yet another aspect of the present invention, the one or more methods of the invention described herein are adapted to a solution based assay as opposed to a low density microarray assays. For example, a refinement of the primary product, the normal variation KMT, is a KMT of copy number variant breakpoints, i.e., the molecular boundaries of these lesions in the population. The KMT allows the detection of copy number changes that are frequent in the population utilizing a rapid PCR (Polymerase Chain Reaction) based method rather than an array-based method. (e.g., FIG. 2). This approach allows for the analysis of hundreds of thousands of individuals for the presence of copy number variants of interest, a scale not feasible currently with microarray analysis.

Determining the presence or absence of a particular variant or plurality of variants in various genes or various loci on a gene in a patient with or at risk for developing a genetic based disorder (e.g., cancer) can be performed in a variety of ways. These tests can be performed using conventional and well known techniques and sources of the genetic material. For example for array or non-array analyses, one can use DNA or RNA collected from biological samples, e.g., tissue biopsies, urine, stool, sputum, blood, sweat, tears, cells, tissue scrapings, breast aspirates, body fluids or other cellular materials, and can be performed by a variety of conventional methods including, but not limited to, PCR, hybridization with allele-specific probes, enzymatic mutation detection, chemical cleavage of mismatches, mass spectrometry or DNA sequencing, including minisequencing. In particular embodiments, hybridization with allele specific probes can be conducted in two formats: (1) allele specific oligonucleotides bound to a solid phase (any conventional material, such as but not limited to, glass, silicon, nylon membranes) and the labeled sample in solution, as in many DNA chip applications, or (2) bound sample (often cloned DNA or PCR amplified DNA) and labeled oligonucleotides in solution (either allele specific or short so as to allow sequencing by hybridization). Diagnostic tests may involve a panel of variants, often on a solid support, which enables the simultaneous determination of more than one variant.

For example, the determination of variant involves determining the sequence of the variant site or sites by methods such as polymerase chain reaction (PCR). Alternatively, the determination of the presence or absence of a kinase activity increasing nucleic acid variant may encompass chain terminating DNA sequencing or minisequencing, oligonucleotide hybridization or mass spectrometry. In one embodiment, the invention provides a method of screening for variants in a test biological sample by PCR or, alternatively, in a ligation chain reaction (LCR) (see, e.g., Landegran, et al., 1988. Science 241: 1077-1080; and Nakazawa, et al., 1994. Proc. Natl. Acad. Sci. USA 91: 360-364), the latter of which can be particularly useful for detecting point imitations in a gene (see, Abravaya, et al., 1995. Nucl. Acids Res. 23:675-682). The method comprises the steps of designing degenerate primers for amplifying the target sequence, the primers corresponding to one or more conserved regions of the gene, amplifying reaction with the primers using, as a template, a DNA or cDNA obtained from a test biological sample and analyzing the PCR products. Comparison of the PCR products of the test biological sample to a control sample indicates variants in the test biological sample. The change can be either and absence or presence of a nucleic acid variant in the test biological sample. Alternative amplification methods include: self sustained sequence replication (see, Guatelli, et al., 1990. Proc. Natl. Acad. Sci. USA 87:1874-1 878), transcriptional amplification system (see, Kwoh, et al., 1989. Proc. Natl. Acad. Sci. USA 86: 1173-1177); Qb Replicase (see, Lizardi, et al, 1988. BioTechnology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

PCR primers may be designed using a number of available computer programs, including, but not limited to Oligo AnalyzerS.O; Oligo Calculator; NetPrimer; Methprimer; Primer3; WebPrimer; PrimerFinder; Primer9; Oligo2002; Pride or GenomePride; Oligos; and Codehop. Detailed information about these programs can be obtained, for example, from www.molbiol.net. In addition, primers may be labeled using labels known to one skilled in the art. Such labels include, but are not limited to radioactive, fluorescent, dye, and enzymatic labels.

Analysis of amplification products can be performed using any method capable of separating the amplification products according to their size, including automated and manual gel electrophoresis, mass spectrometry, and the like. Alternatively, the amplification products can be separated using sequence differences, using SSCP, DGGE, TGGE, chemical cleavage or restriction fragment polymorphisms as well as hybridization to, for example, a nucleic acid arrays. The methods of nucleic acid isolation, amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; $3^{rd}$ edition (Jan. 15, 2001), ISBN: 0879695773. Particularly useful protocol source for methods used in PCR amplification is PCR (Basics: From Background to Bench) by M. J. McPherson, S. G. M011er, R. Beynon, C. Howe, Springer Verlag; 1st edition (Oct. 15, 2000), ISBN: 0387916008.

These normal variation knowledge management tools utilize a consistent and robust platform (i.e. tiling path BAC microarrays or other commercially available arrays) and include typing of at least 100, 1,000, 2,000, 5,000, 7,000 or 10,000 normal individuals from a variety of populations. The KMTs are developed using a systematic, consistent, comprehensive and robust system to generate the core of this technology. While the data generated from different platforms can be considered equivalent, in practice each system has some inherent methodological flaws. However, the system of the invention has a unique strength, such that any samples from any platform can be compared to the normal copy number variation knowledge management tools to distinguish normal from abnormal variations. The KMTs are used to evaluate the genetic profiles from patients to more accurately identify the variations which are linked to a particular disease state. Additionally another aspect of the invention includes manufacturing and selling the products of the aCGH tools in the exact format that the (KMTs) was generated. The arrays for the cCGH are formulated for specific disease states and structured to allow for discrimination among a number of potential diseases with similar symptoms. Additionally, for those who do not wish to perform the experiments themselves, a service is offered to perform the tests employing the same platform that was used to generate the KMTs.

In one aspect of the invention, the KMTs are utilized in a method of identifying the relevance of a copy number variant in a subject, whereby genome-wide screening of a subject is conducted to identify a copy number variant, and subsequently, the variant is compared to a database of normal copy number variants obtained from a population of individuals. The number of individuals is at least 100, 1000, 2000, 3000, 4000, 5000, 6000, 7000, 8000, 9000, 10,000, 20,000, 30,000, 40,000, or 50,000 individuals. Furthermore, the number of normal copy number variants, included within the KMT is at least 100, 200, 300, 400, 500, 600, 700, 800, 900, 1000, 5000, 10,000, 20,000, 50,000, 100,000, 1,000,000, 10,000,000, or 1,000,000,000.

The, array CGH based KMTs (Knowledge Management Tools) enable a cytogeneticist and a diagnostician to accurately diagnose a submicroscopic chromosomal abnormality. This normal variation KMT has flexible compatibility with any type of array CGH platform creating a gold standard for the cytogenetics diagnostic industry.

Hundreds of millions of dollars have been invested in the study of common/complex disorders over the last two decades. The predominant hypothesis which underlies such disorders (schizophrenia, diabetes, obesity, Alzheimer's etc) is the so-called 'polygenic model'. This model assumes the existence of multiple alleles, each of weak effect, which, together, result in the phenotype. Large amounts of funding have been poured specifically into linkage and association studies in complex disorders, however the elucidation of functional SNPs or expression profiling has not paralleled the promises of the Human Genome, International Hap Map, or Japanese Millennium projects Many single gene/single mutation disorders result in phenotypes that fall into the category of complex/common. For example, microdeletions of chromosome 22q11 result in the manifestation of psychosis (schizophrenia) in one third of all affected adults. This represents a 33 fold increased risk for schizophrenia in this condition, relative to the general population risk of 1%. There is general agreement that the sole and relevant genetic change in these individuals is the microdeletion at 22q11. Further examples of specific mutations that result in disorders classically believed to be polygenic are: Congenital Heart Disease, Alzheimer's, Parkinson's disease, and Diabetes.

Congenital Heart Disease is a category of disease that affects 1% of all newborns and which has traditionally been thought to be complex in etiology but which is likely to result from multiple independent genetic lesions in different individuals, each of which has one major mutation. Possibly involved are microdeletions at 22q11.

With Alzheimer's only a few definite genetic lesions are known to be causative which include mutations in the Presenilins. While these are relevant in only a small percentage of all affected individuals, it is likely that similar mechanisms will be found to play a role in the majority of individuals.

In Parkinson's disease mutations in alpha-synuclein have been found in a small number of families. In these individuals, a mutation in that gene alone can account for the disease. This is again, evidence against the polygenic model.

With Diabetes most of what is known points to the involvement of many single gene mutations in different individuals.

Some of the conditions or diseases of importance for screening and further research include autism, coronary artery disease, Alzheimer's disease, Parkinson's, schizophrenia, risk of stroke, diabetes and bipolar disorder. It should be noted that the various embodiments disclosed herein above are not meant to be limiting or exclusive examples of compositions and methods that would otherwise encompass the present invention.

It is believed that the polygenic model, while potentially relevant in some cases, does not need to be invoked universally. The belief is that phenotypes are complex in the sense that individuals with differing, but unique, mutations may all suffer the same end phenotype. This is because the 'space' of phenotypes is much smaller than the 'space' of genotypes. In other words, the number of potential genetic changes that exist is huge, while the number of phenotypes that are recognizable is much more limited in number. Further examples of this phenomenon include mental retardation (for which dozens of genes are already known on the X chromosome alone, and many hundreds await identification on the non-sex chromosomes) and anemia, for which over a hundred causes (both genetic and environmental) are listed in standard medical textbooks.

Although the medically relevant markers are identified and developed from CGH microarrays and included within the KMT, the subsequent diagnostic tests for biomarkers resulting from the comparison of the invention for identifying a particular disease typically are not microarray-based. The biomarkers of significance linked to a particular disease or condition are identified using the KMTs but once identified, the biomarker may be assayed using many conventional assay protocols. For simplicity, cost-effectiveness, manufacturing ease and adequate to equivalent sensitivity, the assays are solution-based. The novel diagnostic assays are a direct outcome of the KMTs which reveal insights into the mechanisms of disease, both common and rare. The business model includes in-licensing of important assays and out-licensing of internally developed assays via out-licensing of the medically relevant loci and sales of the product essential for performance of the assay.

Generated from the normal variation database, is another KMT that sets forth a genome wide copy number breakpoint map. From understanding the precise boundaries of these variants at the molecular level come diagnostic assays for all copy number variants. The copy number breakpoint map identifies normal variants for comparison to the PCR assays of the genome of subjects. Again it permits one to distinguish copy number variation of significance.

An additional aspect of the invention involves research and research services. There are hundreds of research labs around the world utilizing array CGH as a means to associate chromosomal number abnormalities, but are limited to associations that define disease etiology. The normal variation KMTs will be pivotal to these researchers to identify and characterize medically relevant loci, because identifying variations is substantially less significant, if such variations are not compared to variations in the normal population. The KMTs of the present invention will be provided to researchers to permit the building of a "bench to bedside" pipeline of medically relevant biomarkers, by gauging the importance of chromosomal abnormalities in individuals in disease states versus individuals in normal states. Through collaboration with these researchers, more information will be collected, compiled, added to the KMTs and translated through an in-licensed program of medically relevant loci into diagnostic assays in the CLIA lab. Additionally, services will be provided that will permit a researcher to send their collections of patient samples to the CLIA lab for analysis and evaluation. The business methods include licensing the use of the KMTs for those researchers who wish to process their own information, back licenses to receive additional discoveries of biomarkers from the researchers and licenses for the provision of services. These services include analysis of samples using either aCGH or PCR and/or comparison to the KMTs.

Genetic studies in common phenotypes are likely to yield fruit primarily if individuals are investigated on their own merits. In other words, phenotypes need to be subdivided until specific genetic changes in specific individuals are identified. Current studies aim at analysis of mixtures of individuals with (apparently) identical phenotypes but who are likely to differ substantially in terms of the underlying genetic causes. In the case of anemia, this argument is solid. No patient would currently accept a diagnosis of anemia from his or her doctor (without further information on the etiology—iron deficiency (genetic/dietary), folic acid deficiency etc), nor would any funding agency worth it's salt countenance a linkage study in anemia, because the heterogeneity of this phenotype is now widely accepted. Linkage analysis in anemia (i.e., a study of hundreds of individuals with anemia, all lumped together) would likely yield inconclusive results.

Along with continuing to build and expand a knowledge base of copy number variation in the general population, this collaboration and individual research will also yield insights into the underlying etiologies in a range of disorders, depending on which patient samples are collected or acquired for the analysis. The incorporation of array CGH results from collaborators through agreements, allows the additional of anonymous and confidential information, thus adding to the statistical power of the KMTs. The important point is the study of every individual on their own merits, without recourse to the statistical methods implicit in linkage/association studies, wherein individuals with multiple genetic etiologies are likely to have been lumped together. It is believed that genome wide copy number detection is the most robust and efficient method for screening genomes for variation, both normal and potentially associated with disease.

Included in the research is basic research involving the analysis of the genome for gains or losses, that is insertions or deletions, with a comparison to the disease-relatedness. These changes are screened for their potential use as informative biomarkers.

Also, included is clinical research which uses the array CGH in longitudinal studies to provide genomic "snapshots" at various points during the advance of the disease. For example, these snapshots at diagnosis, after treatments with therapeutics, and during relapse provide a better understanding of disease progression as well as an evaluation of the genomic instability associated with the disease. For example, this is particularly useful with certain cancers. This monitoring will improve therapy by assisting in identifying those subpopulations and linking them to the therapy. In addition, the CLIA lab is equipped with the infrastructure to run genome-wide array CGH CLIA regulated clinical studies with the capacity to perform data analysis for others as a contract service.

Translational medicine is another aspect of the invention providing for the transfer of the wealth of new data emerging from the internal normal variation biomarker discovery program and the in-licensed markers (from the research services core program) and translating it into direct benefits for patients. This translational medicine will accelerate the availability of diagnostics by delivering research discoveries to patients as quickly as possible. The CLIA lab is the core facility for continuing to research the genome and associate the conditions and/or diseases and therapies for improved therapy. The CLIA is utilized to perform the analysis of the individuals to continue building and expanding the KMTs, for screening subjects to obtain genomic information for the comparison and for performing any diagnostic assays utilizing biomarkers identified from the comparisons to the KMTs.

Another facet of the invention is predictive and personalized medicine. Healthcare systems recognize that the personalized medicine approach has the greatest potential for treating each patient uniquely, specifically and optimally. The use of the KMTs is key to interpreting chromosomal changes relative to certain disease states. Genes involved in pathological chromosomal variants represent targets for therapeutic treatment and the linkage of the genetic makeup to an isolated population of patients allows personalized treatment. Personalized medicine requires more emphasis on IVD and greater cooperation between diagnostic and therapeutic organizations in the development of new technologies and products but also in review of existing medications. The use of pharmacogenomics and toxicogenomics to compare the patient's sample against the KMTs for copy number variants allows the identification of the most effective drugs for certain patient populations. Included in this evaluation is the genetic basis of the metabolism of drugs, including toxicity, to assist targeted therapies. Evidence is clear and examples abound where array CGH data is used in predictive medicine.

Case study #1. Prognostic Indicator—A group at Sloan Kettering has used the technology as a prognostic indicator to predict the outcome of patients with diffuse large B-cell lymphoma (DLBCL) who will either have a good or poor survival—independent of clinical features that are routinely used. These small genomic regions associated with the outcome may be followed up with gene expression studies and may reveal target genes important in DLBCL.

Case Study #2. Theranostic Development Tool—Tri-locus Test to Predict Drug Resistance in Ovarian Cancer: Berkeley and UCSF conducted genome wide analyses to identify aberrations that are most strongly associated with poor response to treatment with platinum/paclitaxel therapies in ovarian cancer. Comparative Genomic Hybridization (CGH) studies of genome copy number show recurrent amplification in regions at 3 chromosome locations. Berkeley and UCSF have developed markers that can be used in a variety of assaying techniques to detect these amplifications. They have identified amplification of the PVT1 gene as a potential predictor of drug resistant ovarian cancer tumors and a promising therapeutic target. The PVT1 gene maps to the region of amplification at the 8q24 chromosome location that is most strongly associated with reduced survival duration in platinum/paclitaxel treated patients. The transcription levels of PVT1 are highly correlated with DNA copy number alterations in ovarian cell lines and high level amplification and/or over expression of the PVT1 gene are significantly associated with reduced survival time.

Studies employing PVT1 inhibitors reinforce the value of PVT1 as both a predictive marker and therapeutic target for tumors that are not responsive to platinum/paclitaxel based therapies. After treating four cell lines that over express PVT1 with siRNAs that reduce PVT1 transcription, Berkeley Lab/UCSF scientists found that cell proliferation was inhibited. siRNA treatment of cell lines that do not amplify or over express PVT1 did not inhibit growth or induce cell death. These studies indicate that siRNAs or small molecule inhibitors targeting the gene are promising therapies for chemoresistent tumors. Such therapies might be enhanced when combined with platinum plus paclitaxel treatment. This group has developed an array of 48 prognostic BAC clones as markers for predicting poor survival of late stage serous ovarian cancer patients. The regions that the clones span contain sequences located on 13 chromosomes were found to be grade specific markers of poor and good prognosis. The prediction method algorithm is based on the correlation of copy number changes within these 48 regions with patients' outcome.

This technique has been developed using tumor samples from a cohort of 40 patients and was tested on an independent cohort of 30 patients with late stage serous ovarian cancer, where it predicted survival outcome with a 77% success rate. These prior studies were performed on a quite small scale using small numbers of individuals without correlation to normal or abnormal copy number variations.

Personalized medicine is especially relevant in the field of pharmacogenomics. Pharmacogenomics information is especially useful in clinical settings where correlation information is used to prevent drug toxicities. For example, patients are often screened for genetic differences in a gene or chromosomal region, which correlate to a phenotype of medical importance (e.g., disease state). However, only a small percentage of observed drug toxicities have been explained adequately by the set of pharmacogenomic markers available to date. In addition, "outlier" individuals, or individuals experiencing unanticipated effects in clinical trials (when administered drugs that have previously been demonstrated to be both safe and efficacious), cause substantial delays in obtaining FDA drug approval and may even cause certain drugs to come off market, though such drugs may be efficacious for a majority of recipients.

The various biotechnological methods used to date to identify target genomic regions include, for example, differential gene expression which essentially looks for differences in gene expression between control and case samples; protein-protein interaction maps which are used to identify drug receptors and their immediate effectors; and mining human sequence databases for sequences similar to known disease-related, pharmacokinetic or pharmacodynamic regulators. In comparison, association studies that correlate and validate genomic regions with a particular phenotypic trait rely on population genetics and robust statistical metrics. Association studies provide a powerful tool to obtain greater amounts of information in a shorter amount of time thus reducing costs of research and development efforts. However, the present invention provides a more powerful tool than association studies utilized in the relevant art, because any gene/genome variation identified in an individual is correlated to the normal variation database provided by the KMT. In the association studies, a phenotype is correlated to gross genomic information. However, a particular phenotype will typically be a result of numerous genotypes.

The KMTs of this invention allow a finer evaluation of the differences of these genotypes and permit copy number variations to be linked to smaller subpopulations within the larger group and correlated to a particular effect, such as better or worse response to a drug. Therefore, drug treatments can be analyzed for efficacy and toxicity. Indeed, copy number abnormalities are key genetic components which pharmaceutical companies will use to differentiate drug efficacy and adverse reactions in an individual.

Further into the drug commercialization process, drug companies invest hundreds of millions of dollars to develop a new product, only to suffer large losses due to clinical trial participants having unpredictable effects (e.g., increased toxicity or inadequate or no response to the tested drug). In order to overcome negative results, obtain regulatory approval faster and recoup losses, drug companies need to associate effects with genetic profiles of clinical trial participants. It would be very advantageous for drug companies to be able to predict which individuals in a population will tolerate or respond positively to a tested drug, and/or which individuals will experience negative side effects or no significant improvement from the drug.

The drug research and development process includes everything from the discovery of target genomic regions to drug discovery and final product launch. This process is currently very lengthy, expensive and risky. On average, it takes fourteen years to develop a product from the initial research laboratory period to FDA approval. Any event that delays the commercialization or development process of a potential drug can cost the affected company a loss of revenue of up to $1 billion annually. Conversely, any change that can accelerate commercialization or development cycle of a potential drug can bring significant financial benefits to the affected company that implements such changes.

Accelerated time-to-market not only brings the benefit of earlier sales revenues but the expanded market share enjoyed by companies that are the first to enter a segment before its competitors. This is critical, because the period of market exclusivity for the first drug in a new market therapeutic class is typically much shorter than would be desirable. Consequently, marketing expenditures have increased rapidly as companies attempt to maintain or increase market share.

In addition to the time-to-market factors, the odds of any compound successfully making it through all of the steps across fourteen years are miniscule. Statistically, out of 5,000 compounds that begin in pre-clinical development, only five make it to clinical trials, and only one is likely to reach the market. The combination of long development cycles and high failure rates results in an average cost of approximately $500 million for making a successful FDA approved compound. Therefore, business systems and methods that improve the efficiency and timeliness of regulatory approval are greatly valuable.

Pharmaceutical companies have recognized the need to improve research and development efficiency by utilizing genomics in their drug discovery programs. This effort is necessary for companies to match historical revenue growth levels and to meet shareholders' expectations. The drive by pharmaceutical companies for efficiency provides an opportunity for application of genome-wide scanning technologies during both the research and clinical development cycle.

One example of the application of the business systems and methods herein can be found in population segmentation. It is generally acknowledged that most drugs work more effectively for some patients than others. Because this variability in patient response is often poorly understood, pharmaceutical companies may unnecessarily discontinue further drug development, fail to obtain regulatory approvals for promising drug candidates, or if approvals are obtained, be unable to market an approved drug effectively or to obtain approval for third party reimbursement.

Genomic differences have long been recognized as influencing how patients respond to drugs. However, pharmaceutical companies generally have not considered genomic differences between patients in developing and implementing clinical trials or in the marketing of approved drugs. By correlating genomic variation with drug response in clinical trials, it is possible to improve the drug development and marketing process. For example, pharmaceutical companies could use the correlation data from earlier stages of clinical trials to make more informed decisions on whether or not to continue trials, enter later-phases of trials or which patients to enroll in later-stages (e.g., phase III or IV). For example, enrolling patients with genetic predisposition for positive drug response can improve the therapeutic index for these patients and improve the possibility of regulatory approval.

Furthermore, understanding the correlation between genomic differences and drug response can enable pharmaceutical companies to improve drug marketing by identifying segments of the population for whom particular drugs are likely to be more effective than other drugs, and encouraging physicians to preferentially prescribe such drugs to these patients. The business methods include licensing the KMTs to pharmaceutical companies for use during their research and clinical trials to interpret and optimize results as much as possible. Alternatively, there are methods of forming relationships or partnerships with the pharmaceutical companies to engage in research of the genomic features of the patient population in conjunction with developing clinical trials. As a part of the agreement, the business would provide the powerful KMTs and the company would provide additional information gleaned about the genome during the trials and analysis. Marketing to physicians can be accomplished by continuing medical education, peer-review journals, Internet, print advertising or direct sale calls. In addition, by using the information disclosed herein a company can better market a drug by segregating a responder population from a non-responder population, or by segregating a population that encounters negative side effects (or even toxicity) from a population that does not suffer negative effects. This may further allow a company to keep a drug on the market that would otherwise be withdrawn or to reintroduce a drug that has already been withdrawn due to adverse effects.

Drugs are typically developed to interact with a single version of a gene product, e.g., protein or receptor in the human body. A drug may therefore, for example, only be effective in individuals that have a particular variation encoding the specific protein or receptor for which the drug was designed. Individuals, who do not have a genetically caused variation in these regions or in regions involved in the metabolism of the drug, may not respond to the drug or may experience adverse side effects, such as increased toxicity for example.

The methods used by the pharmaceutical industry to develop new drugs and to improve existing drugs may be changed when genetic variations are taken into account. Genetic variations may play a significant role in all stages of research and development and drug discovery. Genetic variation information can also be used to improve drugs already on the market by providing information to better select drugs for a particular patient.

To further illustrate the difficulties solved herein, drugs can interact, directly and/or indirectly, with a variety of different proteins that are encoded and regulated by different genomic regions. Therefore, more than one genomic region can determine how an individual responds to a given drug. The inventions herein can be used to identify such multiple regions. As genetic variations are better understood, it is clear that an individual's response to a given drug is dependent upon that individual's unique genome or more specifically variations within the genome. The information generated can also be used to create diagnostic kits to identify the genomic markers that are linked to conditions, diseases or results with a drug. These tests can be used to diagnose and to predict the best course of treatment.

A practical approach to understanding why different individuals respond differently to the same drug is found in grouping individuals together based upon specific genomic similarities or similar CNV patterns. These genomic similarities can occur between unrelated individuals from different ethnic groups and/or from different geographic regions. The ability to identify and associate genetic variations with a phenotypic state (e.g., disease and drug responses) across the entire genome, entire populations, or subpopulations, can facilitate the entire drug development process and can reduce the time-to-market for therapeutics. For example, genetic profiles of select subsets of patient populations may be used to enable pharmaceutical companies to identify drug targets, focus on potentially better leads and move quicker into screening assays. In addition, better drug targets can also provide for safer, more effective points of therapeutic intervention.

Markets that may be addressed by the business systems and methods disclosed herein include, but are not limited to, evaluation of genetic variations and drug response, evaluation of genetic variations to identify and validate target regions, evaluation of variation and susceptibility to disease, identification of conserved non-coding regions that may contain gene regulatory sequences, evaluation of genetic variations and regulatory regions affecting development, and evaluation of other genotype-phenotype associations with commercial potential, such as in consumer products and agriculture. Potential customers or partners for genome-wide pattern information, conserved region information, patient profiling services and other scientific partnerships include, for example, numerous companies in the pharmaceutical, biotechnology and agricultural industries, as well as academic centers and government research institutes.

Other potential customers or partners for the business methods disclosed herein include, for example, healthcare providers, insurance companies, government entities (e.g., Medicaid, Medicare) and employers or any other entity interested in achieving more economical or effective system for providing or paying for medical or life insurance. Such parties can utilize association studies, for example, to selectively approve expensive drugs to patients who are correlated with a susceptibility to an adverse reaction from a generic drug, evaluate better an individual's likelihood to suffer from disease (or die) prior to underwriting them and selecting more effectively health and life insurance premiums for individuals. These parties may provide funding and/or sample sources for the association studies herein correlated to the KMTs for copy number variations.

The business systems and methods herein further include, for example, the development of DNA-scanning and wafer technology and use of that technology's genome scanning capabilities for identifying commercially valuable genetic regions through research collaboration, and verifying such results using associations studies incorporating the KMTs disclosed herein.

In another embodiment, a result obtained using the methods described herein is used to analyze genomic variants, or diagnose a disease state of an individual, for example, a patient. In a further embodiment, the method of analyzing genomic variants, tailoring personalized drug treatment, or diagnosing a disease, comprises reviewing or analyzing data relating to genomic variants obtained for a subject, such as a patient, and compare such data to the KMTs of the present invention, which provide normal copy-number variant data. A conclusion, often in the form of a report, is then provided to a patient, a health care provider or a health care manager, the conclusion being based on the review or analysis of data regarding a disease diagnosis, predisposition to a condition or disease, genetic counseling regarding genomic findings, or recommendations regarding therapeutic treatment. It is envisioned that in another embodiment that providing a conclusion to a patient, a health care provider or a health care manager includes transmission of the data over a network so that the report is delivered in an electronic format.

Figure 4:
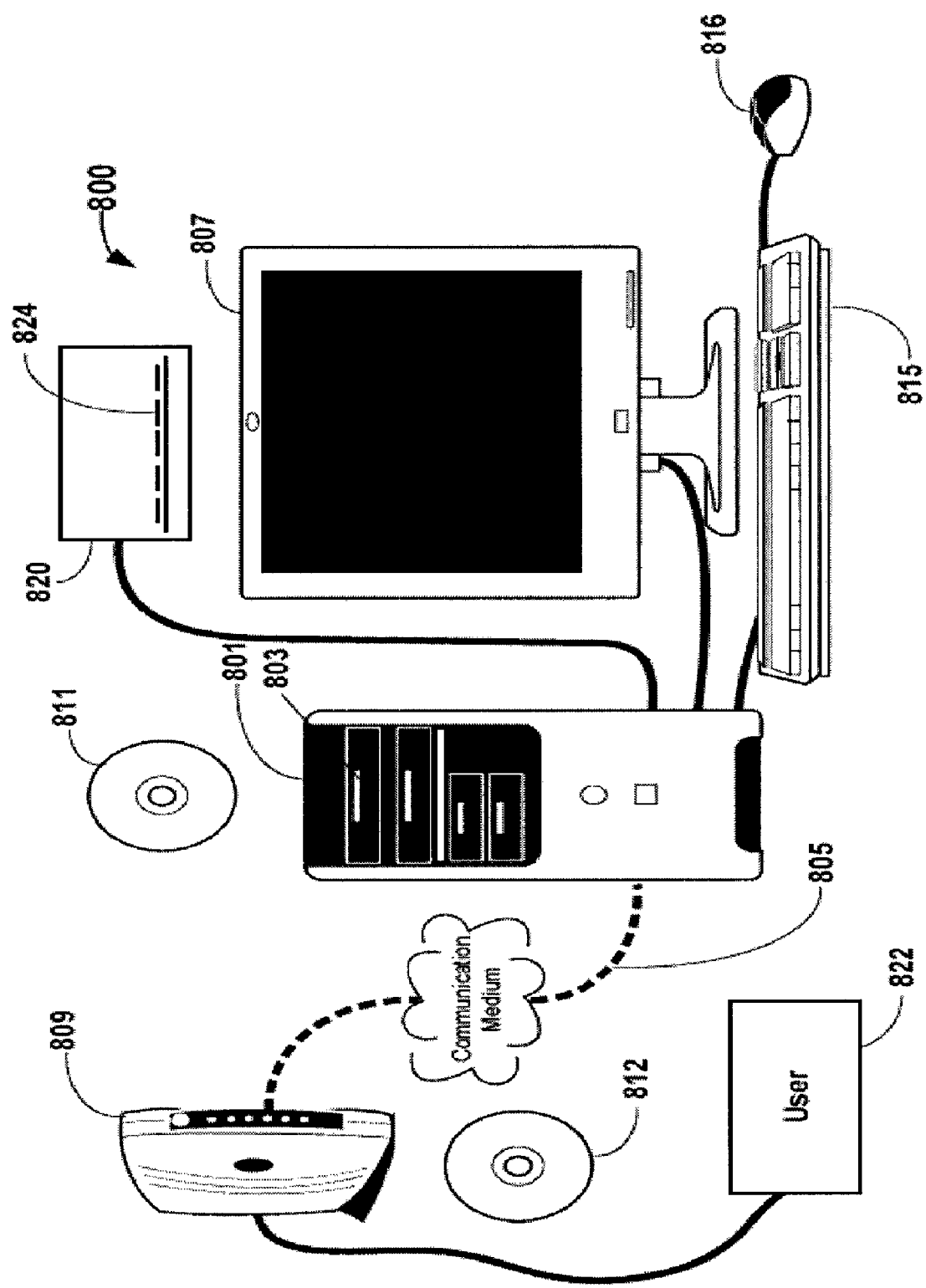
FIG. 4 illustrates an overview of computer-based KMT data management as incorporated in the business methods described herein.

FIG. 4 is a block diagram showing a representative example logic device through which reviewing or analyzing data relating to the present invention can be achieved. Such data can be in relation to a disease, disorder or condition in an individual. FIG. 8 shows a computer system (or digital device) 800 connected to an apparatus 820 for use with the scanning sensing system 824 to, for example, produce a result. The computer system 800 may be understood as a logical apparatus that can read instructions from media 811 and/or network port 805, which can optionally be connected to server 809 having fixed media 812. The system (FIG. 4) includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 822. The receiving party 822 can be a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

In another embodiment, a computer executable logic provides instructions for executing a comparison between the results from a subject on one or more chromosomal abnormalities (e.g., copy number variant). The computer executable logic uses data from the KMTs of the present invention, containing information about the frequencies of copy number variant in a normal population, a statistically significant population, a statistically relevant population, or a population of at least 100, 1000, 5,000, 10,000, 20,000, 30,000, 40,000 or 50,000 individuals. In a preferred embodiment, the computer executable logic uses data from the KMTs to determine if an observed variant in a subject or cohort of subjects correlates to a phenotypic effect, e.g., disease, or correlates to a normal variant, not correlated to a phenotypic effect, e.g., disease. The computer executable logic can be utilized to identify in a subject or groups of subjects the efficacy a particular therapeutic agent, toxicity to a particular therapeutic agent (i.e., stratify patient profiles according to genomic structure variation).

The computer executable logic for determining such correlations is described as comprising an executable code, where the executable code is enabled to perform the method described above, comprising the acts of receiving data for one or more subjects or group of subjects, each providing a set of values or a data set of values; calculating a set of values for each of the data sets associated with each subject or group of subjects; selecting the data model that best fit the data, wherein the best model will be an indication that the frequencies of chromosomal variations observed in a subject or group of subjects as compared to the chromosomal variations so as to provide diagnostics. Such diagnostic determinations include correlations of such variants to phenotypic effects, including disease, disorders, efficacy or toxicity of candidate or actual therapeutic agents. Such determinations can be made by the computer executable logic or an end user, whereby results are displayed to an end user in either electronic or paper format.

Furthermore, any of the information or determinations described herein above (e.g., copy number variant frequencies for subjects, groups of subjects or KMTs providing variant frequency information for a statistically significant or any relevant population) can be stored on a medium capable of allowing computer executable logic. In some embodiments, a computer executable logic product is described comprising a computer usable medium having the computer executable logic (computer software program, including program code) stored therein. The computer executable logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

The KMTs can be provided as a computer program on a computer readable medium with computer executable logic for receiving information from the genome of one or more subjects, for comparing this information against the database of frequencies of normal copy number variations or the copy number breakpoint map (the KMTs) and for providing an output on the assessment or result of the comparison, The databases of information on copy number (KMTs) may be included in the computer program or accessible with the program. Being accessible rather than incorporated allows for easier updates and modifications of the databases.

A computer system which performs the comparisons is also provided and it includes the ability to input subject genomic information concerning copy number variations. Ideally, this information may be supplied in a digital format from the screening assay, either CGH or PCR, directly to the computer system. The computer system also includes or has access to the databases (KMTs), performs the comparison and provides an output result of the comparison.

The business methods allow for the commercialization of the KMTs through licenses for access. Part of the commercial product may be the computer programs for inputting the data, running the most efficient comparisons and providing an output or just the computer program for accessing the KMTs. Frequently, the licenses may include provisions for back-licensing any additional copy number polymorphisms of significance identified with the computer program.

Through collaborations with all of the major pharmaceutical and biotech companies, the R&D lab performs genome wide copy number scans of the company's clinical samples. The genome wide scans are then interpreted using the internal engine of normal variation in the population. The resulting information is copy number polymorphisms associated with efficacy and/or adverse reactions of drugs which may be finely targeted to that particular population of patients. Along with the identification of the polymorphisms are assays designed to test for the presence or absence of those copy umber polymorphisms, which may be used by a pharmaceutical company to stratify patients in respective clinical trials. Alternatively, according to the business model, after performance of the array CGH analysis by others, the CLIA lab performs the data analysis and interpretation using the normal variation engines. Furthermore, the CLIA ill perform clinical assays that are prescribed following data analysis.

A part of the personalized medicine aspect of the present invention includes therapeutic rescue. The pharmaceutical industry faces extremely high risks based on difficult realities.

Some incredible facts about drug efficacy and toxicity emphasize the importance of a better tailored drug treatment regimen. The fifth leading cause of death is adverse drug reaction. Prescribed drugs do not work for patients 40-50% of the time they are prescribed. This translates to $60 billion annually in the U.S. and $20 billion in Japan, spent annually by consumers for ineffective treatments. The majority of potential drug candidates in a pharmaceutical company's clinical trial pipeline will never make it through the regulatory approval process because of lack of efficacy in enough patients or because of adverse effects in too many patients. This fact is a driver in the ever escalating costs for drug development and the consequent lost billions in development expenditures. A significant percentage of therapeutic responders or those that do not manifest adverse reactions are deprived of effective medicines when a drug does not gain regulatory approval based on traditional clinical trial design, where patients with genetic differences are lumped together with phenotype similarities. Therapeutics already on the market have a high risk of hurting patients because patient surveillance cannot easily be performed. The potential indirect medical costs, (i.e. hospitalization) for patients having relied on a medicine only to experience an adverse effect or lack of efficacy is a staggering financial figure.

All of these facts underscore the value of the KMTs which permit better evaluation of the genetic makeup of the patients and more focused treatment based on their genetic profile. It is broadly accepted that an individual's genetic makeup is responsible for differentiating a drug responder from a non-responder. It is also clear that an individual's genetic makeup is responsible for differentiating one's level of adverse effects to a particular drug therapy. Therefore, patient screening utilizing KMTs of the present invention provides for an effective evaluation distinguishing the important variations from those that do not have an effect on the phenotype and disease, or drug therapy. By utilizing all of this information, the cytogeneticist will generate a diagnostic recommendation from the KMTs. The advantage of the KMTs is their flexible and universal architecture allowing compatibility with other systems for data analysis and interpretation.

A critically important aspect of this linkage is the rescue of drugs from clinical trials by using the KMTs to better stratify patients based on their genome and identify effective therapeutics for possibly smaller groups of patients. This rescue is possible in both pre-market and post-market drugs to provide useful drugs which otherwise might have been abandoned and the patients not treated. The drugs after approval, such as by the FDA, can be evaluated and patients screened to continue segmenting the patients based on response as they progress through stages of disease progress, plateau or improve.

Additional products include CGH microarrays, reagents and downstream analysis tools. The microarrays are optimized for use in conjunction with the KMTs and are designed to focus on different disease states. The microarrays are provided as stand alone products or in conjunction with licenses to access the KMTs. As a result of the internal copy number polymorphism discovery program another product is a portfolio of medically relevant bio-markers. These markers are a stand alone medically relevant marker which can be utilized a diagnostic service performed in its own CLIA lab. The markers are also manufactured and available as a fully developed assay to be utilized directly by diagnostic reference labs or authorized service providers in the U.S. or countries abroad. These assays can be PCR-based or alternative amplification and detection methodologies are provided. Another alternative is as an out-license for the medically relevant biomarker to platform companies with unique technology platforms which are established in the diagnostic community as turnkey methodologies.

The second of major pipelines contributing to the services menu for CLIA lab will come from the internal bio-marker discovery program. The investments made in the internal bio-marker discovery program will be driven by market potential. A partial listing of assays of interest are: Autism Coronary Artery Disease Alzheimer's Disease Parkinson's Schizophrenia Risk of Stroke Diabetes Bipolar Disorder Services of the CLIA facility will be sold domestically by a direct sales force. Strategic Alliance alternatives such as co-marketing agreements with national labs may be considered as a means for establishing nationwide reach to prescribing physicians.

Assays developed internally will be sold internationally to authorized service providers through relationships created by business development. A model for building medical relevance as a consensus in the prescribing community will be built. This is a comprehensive plan in and of itself. However, in general it will encompass the involvement via collaborations with consortiums of physicians in the specialty areas that pertain to the medical practices respective of the diagnostic application. These will be higher level business and corporate development activities.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLES

Example 1

Breakpoint Analysis

Despite the description of many hundreds of copy number polymorphisms and inversions, to date very few have been analyzed in enough detail to allow determination of the precise boundaries at the molecular level Where a given deletion/duplication/inversion/translocation, which is believed to be a benign polymorphism in the normal population, has been studied, it has been found that the molecular breakpoints are identical in unrelated individuals. For example, it was determined that a common microdeletion polymorphism on chromosome 8q24.3 has identical breakpoints in 100 unrelated individual studied thus far. Furthermore, recent work on a common inversion polymorphism in Europeans has demonstrated identity in unrelated individuals and is consistent with a single origin of this variant (Gilling et al. 2006).

If a variant is benign, then it is likely to be transmitted in families. Thus, the chromosome 8q24.3 microdeletion described above is inherited in a straightforward Mendelian fashion in all families so far observed. There is little or no selection against the presence of the variant. As a corollary, variants that are strongly associated with disease are sporadic (i.e., not inherited). A good example is Williams syndrome, associated with a deletion at 7q11.23—this is a severe neurodevelopmental disorder, which is nearly always (>99%) seen to occur in an individual child within an otherwise normal family. Such deletions arise de novo in >99% of cases. The rate of de novo genomic changes (at the level of deletions/duplications) is relatively low in normal individuals. In other words, it is believed that a normal child will have very few de novo deletions/duplications in their genome, when compared to their parents.

As such, copy number variants will each have arisen as unique events in some founder individual (as in the case of the European inversion cited above). Furthermore, it follows that the rates of given variants will be dramatically different in different populations. For example, the 8q24.3 deletion mentioned above, which is present at 5% in Caucasians is present at significantly lower levels in Chinese and African-Americans.

Given that 'benign' copy number variants will have identical molecular boundaries in different individuals, PCR assays can be utilized to identify endpoints. Breakpoint analysis in copy number variants can be achieved in a number of ways: The variant chromosome can be isolated in somatic cell hybrids by fusing the human parental cell with a rodent cell line and then testing subclones for the presence of the variant chromosome in the absence of the wild-type chromosome (the majority of variants are heterozygous). Once the variant chromosome is isolated, fine mapping analysis is conducted, in the absence of the wild-type chromosome, in a straightforward manner. This 'conversion of diploidy to haploidy' is recognized in the relevant art as important in the analysis of heterozygous mutations. Indeed, commercial applications have been implemented based on diploid/haploidy conversion (GMP Genetics, Inc.). However, such applications are based somatic cell hybrid analysis, which is robust but time-consuming and labor intensive.

Figure 2:
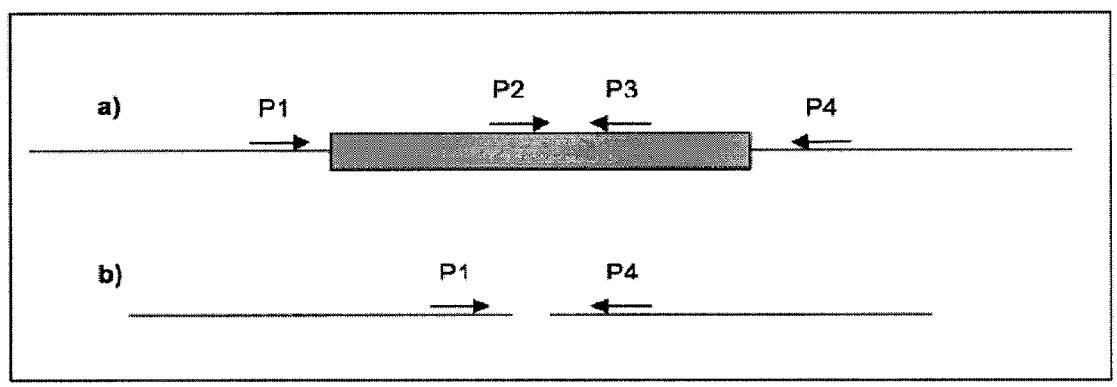
FIG. 2 depicts a schematic demonstrating a junction fragment PCR assay. a) Normal allele: P2 and P3 amplify a 420 bp PCR product; P1 and P4 flank a ~182,400 bp region and do not generate; b) Deleted allele: P1 and P4 amplify a 300 bp PCR product; N/N: 420 bp/420 bp; N/Δ: 420 bp/300 bp; Δ/Δ: 300 bp. ▬: Deleted region (182,088 bp in length); Δ: Deletion; N: non-deletion; P: primer
Figure 3:
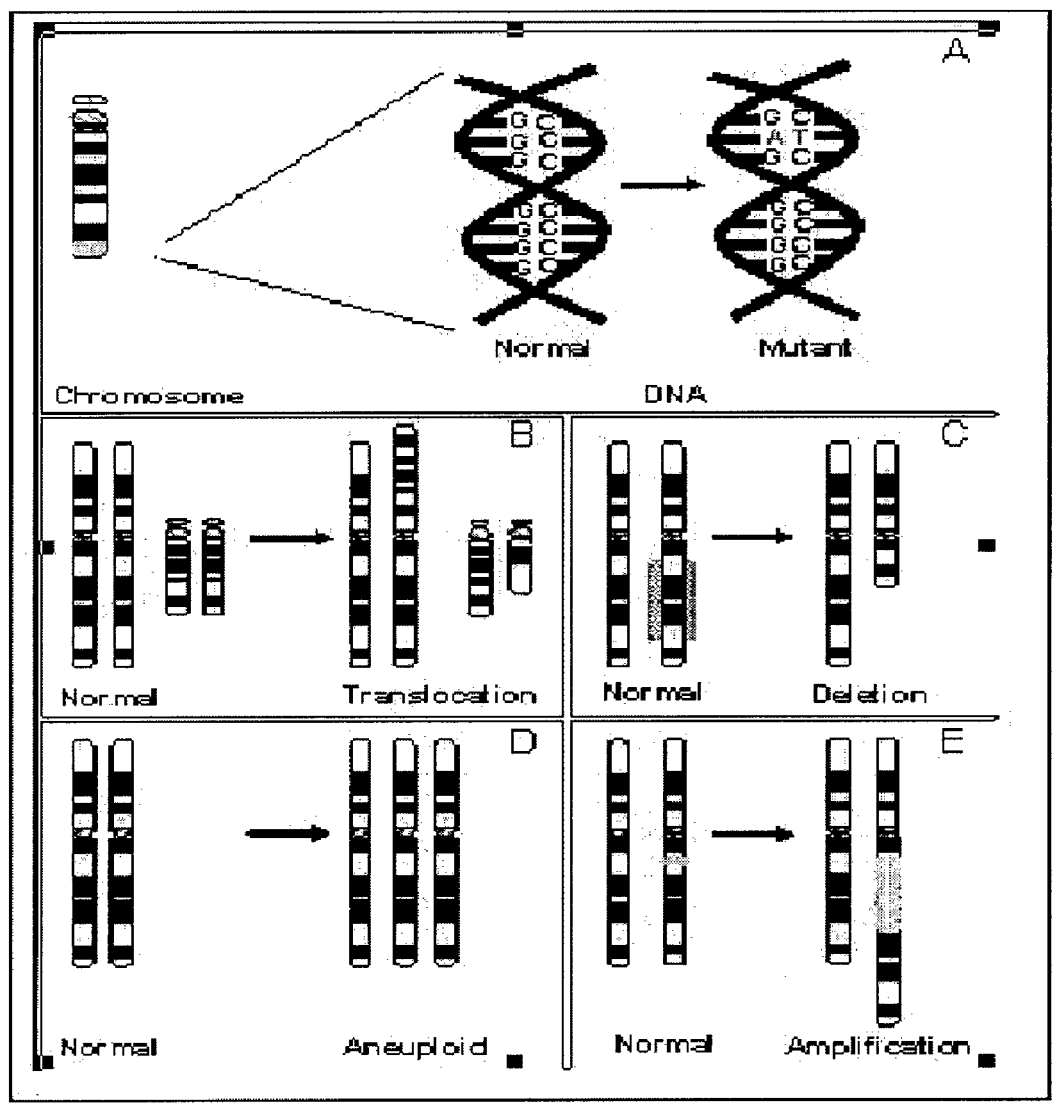
FIG. 3 illustrates some common genetic changes: A. Mutation. One nucleotide base is substituted for another in the DNA leading to encoding of abnormal protein B. Translocation. Chromosomes exchange segments by breakage through specific genes and reunion of broken ends. The genes thus disrupted encode aberrant proteins C. Deletion. Loss of a chromosomal segment (or gene) caused by breaks in the chromosome and rejoining of broken ends. Loss of a gene abrogates its function. D. Aneuploid. Extra copy of an entire chromosome leads to increased expression of many genes on it and disrupts normal balance of gene expression. E. Amplification. Amplification of a gene leads to vastly increased expression of the protein encoded by it.

With modern methods of creating custom oligonucleotide arrays (Agilent, NimbleGen, CombiMatrix), it is possible to generate an array that specifically interrogates the approximate endpoints of the variant, at extremely high resolution (down to 1 bp). While copy number calls cannot accurately be made on the basis of the behavior of an individual oligo, they can be made by reference to averaging windows and segmentation analysis, so that PCR primers can be designed for the purpose of amplifying a novel 'junction fragment' at the boundary endpoints. (FIG. 2: primers P1-P4).

Such primers can be designed utilizing conventional methods in the art. Basically, this step requires preparing several pairs of oligomers, one member of which contains a primer that specifically hybridizes with sequences in the DNA flanking the breakpoint (i.e., lesion) and the second member containing a primer that hybridizes to some part of a gene situated on the other side of the breakpoint, followed by amplifying the DNA by PCR (FIG. 2). Primer design methods are conventional in the art and are provided in the disclosures of the following patent documents: WO 2002/99129; U.S. Pat. No. 6,423,499; U.S. Pat. No. 6,146,834; U.S. Pat. No. 6,251,607; US 2005/0037414; U.S. Pat. No. 6,892,141.

For example, a tiling oligo array designed around a copy number change on chromosome 3p was utilized to achieve such mapping (Nittler et al. 2005; describing tiling oligo array). Simple sequencing of such PCR amplified junction fragments reveals the precise molecular boundaries of a variant.

Once the molecular boundaries are known for a variant, a simple PCR assay, at minimal cost, can detect the presence of the variant in genomic DNA obtained from a test subject or patient, without the added step/cost of resorting to an array experiment. For example, primers can synthesized on an Applied Biosystems (Foster City, Calif.) DNA synthesizer (Gelmann et al, 1983, Nature 306:700: Bernard et al, 1983, EMBO J 2:2375; Petrini et al, 1987, J. Immunology 138: 1940). Template DNA can be isolated from a subject utilizing conventional methods in the art. Subsequently, a template DNA (e.g., 200 ng) is subjected to PCR essentially as described by Saiki et al (1988, Science 239:487). Amplification with Taq (*Thermus aquaticus*) polymerase can be in 100 µl reaction mixtures containing the DNA in 50 mM KCl, 10 mM Tris-HCl (pH 8.3 at room temperature), 1.5 mM MgCl$_2$, 0.01% gelatin (w/v), each primer at 1 µM, each dNTP (dATP, dCTP, TTP, dGTP) at 200 µm. The samples were heated to 95° C. for 2 minutes, cooled to room temperature (about 22°-24° C.) prior to adding 2 units of polymerase and subjected to 25-30 cycles of PCR. Amplicons can subsequently be sequenced using methods conventional in the art.

For example, sequencing is performed by ABI automated fluorescent sequencing machines and fluorescence-labeled DNA sequencing ladders generated via Sanger-style sequencing reactions using fluorescent dideoxynucleotide mixtures. PCR products are purified using Qiagen QuickSpin columns, the Agencourt AMPure PCR Purification System, or PCR product purification kits obtained from other vendors. After PCR products are purified, the nucleotide concentration and purity is determined with a Nanodrop 7000 spectrophotometer, and the PCR product concentration is brought to a concentration of 25 ng/µl. As a quality control measure, only PCR products that have a UV-light absorbance ratio ($A_{260}/A_{280}$) greater than 1.8 are used for sequencing. Sequencing primers are brought to a concentration of 3.2 pmol/µl.

An important aspect for utilizing junction fragment PCR, as described herein above, is that PCR is much more rapid and efficient in terms of ease of use, time and cost in detecting a given copy number change in many individuals as compared to other platforms. Given that 'benign' copy number variants will have identical molecular boundaries in different individuals, PCR breakpoint genome wide analysis provides a much faster and less costly assay. For example, one can consider the requirements for determining the 8q24.3 deletion status in 10,000 individuals. If an array based approach is used for the determination of this specific variant (8q24.3 deletion) in a cohort of interest, and not a genome-wide analysis, then a conservative estimate of the cost is 10,000× $300 (per array, including labeling costs etc—a very conservative estimate)=$3,000,000, which is quite prohibitive.

In sharp contrast, if determination were by PCR, using the specific assay designed to interrogate the endpoints, described herein above, the cost would be many orders of magnitude less. For example, the cost for each PCR reaction is less than about $1 (i.e., $1 for PCR versus $300 for array). Another important consideration is that breakpoint analysis will be eminently suitable for third world situations/studies, where aCGH really is impractical technically and financially. However, for global genomic analysis, alternative platforms, such as arrays, are necessary.

Example 2

Array-Based Comparative Genomic Hybridization

It will at once be evident to one of skill in the art, BAC arrays are but one method for copy number variation analysis. As described in the relevant art and herein above, alternative platforms are available for analysis of copy number variations (e.g., different array formats; Agilent, Affymetrix, NimbleGen, etc.). A key aspect is that the KMTs of the present invention can utilize alternative platforms or modified existing platforms to compile the normal variation database.

Genomic DNAs, can be isolated from blood lymphocytes of 10,000 normal, healthy individuals (50% female; 50% male) to provide DNA—reference or normal variation DNA. As needed, the first few samples obtained will be used for array validation. Additional genomic DNAs can be isolated from subjects with FISH-verified known microdeletion syndromes, from subjects with dysmorphisms of unknown etiology, or from subjects without any detectable phenotype suggesting a chromosomal abnormality. Subjects may be screened by a clinical geneticist and undergo a diagnostic work-up, including routine chromosome analysis without a diagnosis (e.g., checklist developed by de Vries et al. (2001)). Genomic DNAs from reference or test subjects can be isolated and purified using a QIAamp kit (Qiagen), according to the instructions of the manufacturer.

Clone Set.—A set of well-characterized, colony-purified, and FISH-verified BAC clones can be used for array construction. There are several available BACs libraries. (e.g., RPCI). The BACs can be derived from the RPCI BAC library used as the main intermediate substrate for the sequencing and mapping of the human genome (Osoegawa et al. 2001). The set can include 32,000 clones selected through a collaboration with other available clone sets (e.g., the Children's Hospital Oakland Research Institute, BACPAC Resources Center, and several other groups to cover the genome with a 1-Mb resolution (Cheung et al. 2001). The key point is that BAC arrays can be selected and combined from various sources. Further, the compilation of BAC arrays is selected so as to provide high resolution detection (100 kb). For example, a tiling path BAC array clone set can will provide such a level of resolution. Additional clones can be added to the array, resulting in an even higher-resolution coverage of genomic regions (e.g., regions known to be involved in a particular abnormality, disease or condition), including the subtelomeric regions of all human chromosomes (77 clones) (Knight et al. 2000) and regions associated with known microdeletion syndromes (30 clones). Finally, particular chromosomes of interest can be covered with a higher density through the addition of clones used in previous studies (Veltman et al. 2003b; Zafarana et al. 2003).

Array Preparation. Genomic target DNAs can be isolated from 12-ml bacterial cultures using Qiagen R.E.A.L. Prep 96 BioRobot kits on a Qiagen BioRobot 9600 (Qiagen), following the instructions of the manufacturer. Degenerate oligonucleotide-primed (DOP) PCR or ligation mediated PCR (LM-PCR) can be performed on isolated DNA from all clones, essentially as described elsewhere (Telenius et al. 1992), with minor modifications (Veltman et al. 2002). DOP-PCR and LM-PCR are conventional in methodologies in the relevant art. Taq2000 (Stratagene) may be used as a thermostable polymerase. DOP-PCR products can be dissolved at a concentration of 1 mg/ml in a 50% DMSO solution and robotically spotted in triplicate onto CMT-GAPS coated glass slides (Corning, UltraGaps) using an OmniGrid 100 arrayer (Genomic Solutions). The array will consist of subgrids and replicates are rinted in different subgrids across the array.

Labeling and Hybridization. Labeling and hybridization can be performed essentially as described elsewhere (Veltman et al. 2002). In brief, genomic DNA can be labeled by random priming with Cy3-dUTP or Cy5-dUTP (Amersham Biosciences). Samples can be mixed with 120 μg Cot-1 DNA (Roche), coprecipitated, and resuspended in 130 ml of a hybridization solution containing 50% formamide, 10% dextran sulfate, 2×SSC, 4% SDS, and 10 mg/ml yeast tRNA (Invitrogen). After denaturation of probe and target DNA, hybridization and posthybridization washing procedures can be performed using a GeneTAC Hybridization Station (Genomic Solutions), according to the manufacturer's instructions. In brief, an 18-h hybridization with active circulation of the probe is performed, followed by five posthybridization wash cycles in 50% formamide/2×SSC at 45° C. and five wash cycles in phosphate-buffered saline at 20° C. Slides were dried by centrifugation after a brief wash in water.

Image Analysis and Processing. Slides can be scanned and imaged on commercially available scanners (e.g., Axon scanners). The acquired microarray images can be analyzed using GenePix Pro 6.0—(Axon Instruments), as described elsewhere (Veltman et al. 2002). For all further analyses, the median of the pixel intensities minus the median local background can be used for every spot on the array (Cy3 and Cy5, calculated separately). Data normalization can be performed in the software package SAS version 8.0 (SAS Institute) for each array subgrid, by applying Lowess curve fitting with a smoothing factor of 0.1 to predict the log 2-transformed test-over-reference (T/R) value on the basis of the average logarithmic fluorescent intensities (Cleveland 1979). This smoothing factor can result in the lowest percentage of false positive results while not increasing the amount of false-negative results in the validation experiments. A consequence of this smoothing procedure is that the ratios of the clones with a copy-number gain or loss are closer to the normal range of log 2 ratios than in normalization procedures without this smoothing.

Quality Control. Clones with an SD of the triplicates >0.3 can be excluded in individual experiments, as well as clones with fewer than two replicates remaining after such analysis. Statistical analysis available in the art can be utilized to determine spot quality (e.g., BlueGnome, BlueFuse, or any other software/hardware package designed for aCGH analysis). Excluded from all experiments are clones that did not show reliable hybridization results in at least four of the five normal-versus-normal control experiments. Clones that mapped to the sex chromosomes (e.g., n=163) are not analyzed in detail. Thresholds for copy-number gain and loss can be determined by examining the results of the control experiments and of previously published work and were set at log 2 T/R values of 0.3 and -0.3, respectively. Experiments were excluded when 15% of the clones showed intensity ratios outside of these regions. Of the 40 experiments performed in this study, 5 experiments did not meet these quality criteria. These experiments were successfully repeated. The final data set is available as a downloadable electronic supplement via the online version of this article.

Analysis of Replicate Experiments. In addition, a dye-swap experiment for each case (patient or control) can also be performed. For statistical analysis of these two experiments, a two-dimensional assay in the software package SAS version 8.0 (SAS Institute) can be used, in which reference regions are calculated containing 99.999% of the data points (P p 0.99999), assuming that the pairs of normalized ratios follow a bivariate normal distribution (FIGS. 1B and 1D). Under the assumption of no deleted or duplicated regions, the number of data points outside the resulting ellipse is expected to be 1/100,000 # the number of clones on the array—in our case, 1/100,000 #3,343 p 0.03. Clones represented by data points outside this reference region in the scatterplot are candidates for a microduplication or deletion event. However, since a dye-swap experiment may be performed for each case, the data points also have to be located in the correct quadrant of the scatterplot (i.e., a positive sign for experiment 1 [patient 1 vs. control 1] and a negative sign for experiment 2 [control 1 vs. patient 1] indicates a potentially duplicated clone, whereas a deleted clone shows opposite signs in both experiments). The a priori thresholds for copy-number gain (log 2 T/R value 0.3) or loss (log 2 T/R value>0.3) are therefore integrated into the scatterplot to indicate the candidate clones for microdeletion or duplication events.

FISH Validation Experiments. FISH validation experiments can be performed on metaphase spreads prepared from patient-derived cell lines using routine procedures. Probe labeling, slide preparation, and hybridization can be carried out essentially as described elsewhere (de Bruijn et al. 2001). A Zeiss epifluorescence microscope, equipped with appropriate filters, can be used for visual examination of the slides. Digital images are captured using a high-performance cooled CCD camera (Photometrics) coupled to a computer. Image software (e.g., Image FISH software package (Intergen)) can be used for analysis of the FISH images. Inverted images of DAPI-stained slides can also be used for chromosome identification.

Results. The output data from the preceding aCGH anaylsis of 10,000 individuals will provide a database of normal copy number variations which can be used in the KMTs of the present invention to provide genomic assessments for a test subject or patient or groups of the same, in diagnosing disease or designing therapeutics.

Example 3

Comparative Analysis

Once the reference database is compiled, similar algorithms can be utilized to generate copy number data from test subjects as from the cohorts used to create the normal variation databases. For the database described in the Example above, such analysis will allow for direct comparison of the results on a given individual with the normal expected variation in 10,000 individuals of the same ethnic group.

For example, MySQL or similar applications can be utilized to create the normal variation databases, using phpmyadmin as a front end. MySQL is a multithreaded, multi-user, SQL Database Management System (DBMS) with an estimated six million installations. MySQL AB makes MySQL available as free software under the GNU General Public License (GPL), but is also dual-licensed under traditional proprietary licensing arrangements for cases where the intended use is incompatible with the GPL. In addition, MySQL works on many different platforms—including AIX, BSDi, FreeBSD, HP-UX, GNU/Linux, Mac OS X, NetBSD, Novell NetWare, OpenBSD, OS/2 Warp, QNX, SGI IRIX, Solaris, SunOS, SCO OpenServer, SCO UnixWare, Tru64, Windows 95, Windows 98, Windows NT, Windows 2000, Windows XP and more recent versions of Windows. Furthermore, ORACLE or other databases can also be utilized.

The databases will contain the aCGH results compiled for the selected number of subjects (e.g., 10,000, as in Example 2, above), including the statistical output of whichever software package is applied (BlueFuse, GenePix Pro etc). Data will be compiled into various MYSQL tables and these tables will be extensively indexed. In addition, secondary tables will be created that will allow for internal normalization of aCGH derived ratios. For example, where an aCGH experiment has been conducted, which is sex-mismatched (male vs. female), ratios will be normalized within such a category. Thus, any ratios on autosomes that are skewed because of homology of the relevant autosomal region to one of the sex chromosomes, will be evened out after normalization. Furthermore, ratios for the sex chromosomes will be normalized, so that calls can be made on the sex chromosomes, even when the experiment was conducted as a sex-mismatched one.

Of course, a substantial amount of data will be from sex-matched experiments, which will more easily facilitate to identify ("calls") changes on the sex chromosomes and elsewhere. The use of sex mismatching has been popular in the field, because it allows for confirmation that the experiment has worked (i.e., by observing the ratios of the X and Y).

For example, if a test subject that has been found to harbor 5 copy number variants, A-E, for each one, a search will be made in the database of the frequency of occurrence of that change within the relevant, ethnically matched, cohort. Depending on the result, a statistical likelihood is provided that the observed copy number variant is significant in the etiology of the test subject's disease (See, Table 1, supra).

Therefore, an exemplary report for such a test subject would be:

TABLE 2

| Test subject variants | Frequency in db |
|---|---|
| A | 5% |
| B | 2% |
| C | 10% |
| D | 1% |
| E | 0% |

Such a report could also be interpreted in the light of other clinical details. If the test subject has a rare genetic disorder, the obvious implication is that variant E should be considered causal. However, in the case of a rare genetic disorder, the responsible clinician can collect further cases of the rare disorder and test them directly for the presence of variant E. In the case of a common disorder, such as diabetes, the variant would be important as well, because said variant can be a very rare cause of diabetes, but one that yields dramatic insights into etiology. Statistical analysis will play an important role in the analyses described above, but without the KMTs and reference database of the invention, identifying the significance of a variant is not possible.

In summary, the databases will comprise cohorts of 10,000 normal individuals from differing ethnic groups, using complementary but different platforms. Statistical thresholds will be used to define copy number changes. These thresholds will vary from platform to platform. Copy number variants in a test subject will be compared directly to the occurrence of those variants in the databases (matching ethnically). Furthermore, the output will be a list of variants in the subject, together with a frequency of those variants in the databases. Significance of the variant in the subject will be via statistical considerations, as outlined above.

What is claimed is:

1. A method of determining relevance of a copy number variant in a subject to a disease or a condition associated with a genotype comprising:

(a) screening a subject's genome with PCR, array Comparative Genomic Hybridization, sequencing, SNP genotyping, or Fluorescence in Situ Hybridization to provide information on one or more copy number variants;

(b) comparing via a computer, information of said one or more copy number variants from the genome of said subject to a compilation of data comprising frequencies of copy number variants in at least 1,000 normal subjects; and (c) determining a statistical significance of said one or more copy number variants from the comparison of step (b) to a condition or disease associated with a genotype or determining whether a copy number variant is present in said subject but not present in said compilation of data from the comparison of step (b), wherein said computer comprises computer executable logic that provides instructions for executing said comparison.

2. A method of determining relevance of a copy number variant in a subject to a disease or a condition associated with a genotype comprising:
(a) screening a subject's genome with PCR, array Comparative Genomic Hybridization, sequencing, SNP genotyping, or Fluorescence in Situ Hybridization to provide information on one or more copy number variants;
(b) comparing, information of said one or more copy number variants from the genome of a subject to a compilation of data comprising frequencies of copy number variants in at least 100 normal subjects, wherein said data comprises a copy number breakpoint map, and
(c) determining the statistical significance of said one or more copy number variants from the comparison of step (a) to a condition or disease associated with a genotype or determining whether a copy number variant is present in said subject but not present in said compilation of data from the comparison of step (b).

3. The method of claim 1 or 2, wherein said compilation comprises data from at least 10,000 normal subjects.

4. The method of claim 1 or 2, wherein said data is genome-wide.

5. The method of claim 1 or 2, wherein said subject is a patient, further comprising designing a therapeutic regimen for said patient by determining that a therapeutic should be excluded from a regimen based on the comparison of step (b).

6. The method of claim 1 or 2, wherein said subject is a patient, further comprising designing a therapeutic regimen for said patient by identifying a therapeutic as efficacious for said subject based on the comparison of step (b).

7. The method of claim 1 wherein said data comprises a copy number breakpoint map.

8. The method of claim 1 or 2, further comprising amplification of a junction fragment of at least one copy number variant.

9. The method of claim 1 or 2, wherein said compilation comprises data from at least 5,000 normal subjects.

10. A computer program product comprising a computer readable storage medium having computer program logic recorded thereon for enabling a processor to determine the relevance of one or more copy number variants in the genome of a subject to a disease or a condition associated with a genotype, said computer program logic comprising:
(a) a receiving procedure that enables the processor to receive a set of information comprising frequency data for copy number variants from the genome of at least 1,000 normal subjects and copy number information from the genome of said subject,
(b) a comparing procedure to compare input data from the genome of said subject against said set of information and,
(c) an output procedure to provide a statistical significance of said copy number information from the genome of said subject based on the comparison of step (b) to a condition or disease associated with a genotype or determining whether a copy number variant is present in said subject but not present in said set of information based on the comparison of step (b).

11. The computer program product of claim 10 wherein said set of information is from the genome of at least 10,000 normal subjects.

12. The computer program product of claim 10 wherein said set of information comprises a copy number breakpoint map.

13. The computer program product of claim 10, 11 or 12 wherein said set of information is genome-wide.

14. A computer system for determining the relevance of a copy number variant in a subject to a disease or a condition associated with a genotype, comprising a computer readable storage medium; having computer program logic recorded thereon, wherein said computer program logic comprises instructions, which comprise:
(a) input instructions for receiving a set of information comprising frequency data for copy number variants from the genome of at least 1,000 normal subjects and copy number information from the genome of said subject,
(b) comparison instructions for comparing the copy number information from the genome of a subject against said set of information and
(c) output instructions for providing a statistical significance of said copy number information from the genome of said subject based on the comparison of step (b) to a condition or disease associated with a genotype or determining whether a copy number variant is present in said subject but not present in said set of information based on the comparison of step (b).

15. The computer system of claim 14 wherein said input instructions are adapted to accept the digital results stemming from an analysis of said subject's genome with array Comparative Genomic Hybridization.

16. The computer system of claim 14 further comprising instructions adapted to accept the digital results stemming from an analysis of said copy number variant with PCR.

17. The computer system of claim 14 wherein said set of information comprises the frequency information for at least 10,000 normal subjects.

18. The computer system of claim 14 wherein set of information comprises a copy number breakpoint map.

19. A computer program product comprising a computer readable storage medium having computer program logic recorded thereon for enabling a processor to determine the relevance of one or more copy number variants in the genome of a subject to a disease or a condition associated with a genotype, said computer program logic comprising:
(a) a receiving procedure that enables the processor to receive a set of information comprising frequency data for copy number variants from the genome of at least 100 normal subjects and copy number information from the genome of said subject, wherein said set of information comprises a copy number breakpoint map,
(b) a comparing procedure to compare input data from the genome of said subject against said set of information and,
(c) an output procedure to provide a statistical significance of said copy number information from the genome of said subject based on the comparison of step (b) to a condition or disease associated with a genotype or determining whether a copy number variant is present in said subject but not present in said set of information based on the comparison of step (b).

20. A computer system for determining the relevance of a copy number variant in a subject to a disease or a condition associated with a genotype, comprising a computer readable storage medium; having computer program logic recorded thereon, wherein said computer program logic comprises instructions, which comprise:
(a) input instructions for receiving a set of information comprising frequency data for copy number variants from the genome of at least 100 normal subjects and copy number information from the genome of said subject, wherein said set of information comprises a copy number breakpoint map, (b) comparison instructions for comparing the copy number information from the genome of a subject against said set of information, and (c) output instructions for providing a statistical significance of said copy number information from the genome of said subject based on the comparison of step (b) to a condition or disease associated with a genotype or determining whether a copy number variant is present in said subject but not present in said set of information based on the comparison of step (b).

21. The computer system of claim 16, wherein said PCR comprises amplification of a junction fragment of at least one copy number variant.

22. The computer system of claim 14 wherein said set of information comprises the frequency information for at least 5,000 normal subjects.

23. The computer program product of claim 10 or 19 wherein said set of information is from the genome of at least 5,000 normal subjects.

24. The method of claims 1 or 2 wherein said screening a subjects genome is by array Comparative Genomic Hybridization.

25. The computer program of claim 10 wherein said receiving procedure is adapted to accept the digital results stemming from an analysis of said subject's genome with array Comparative Genomic Hybridization.

* * * * *